(12) United States Patent
Miller et al.

(10) Patent No.: US 7,876,110 B2
(45) Date of Patent: Jan. 25, 2011

(54) METHOD AND APPARATUS FOR SIMULATING ELECTRICAL CHARACTERISTICS OF A COATED SEGMENT OF A PIPELINE

(75) Inventors: Scott Downing Miller, Dripping Springs, TX (US); Thomas James Davis, Issaquah, WA (US); Jaime Paunlagui Perez, Dhahran (SA)

(73) Assignee: Saudi Arabian Oil Company, Dhahran (SA)

(*) Notice: Subject to any disclaimer, the term of this patent is extended or adjusted under 35 U.S.C. 154(b) by 324 days.

(21) Appl. No.: 12/291,527

(22) Filed: Nov. 10, 2008

(65) Prior Publication Data

US 2010/0116419 A1     May 13, 2010

(51) Int. Cl.
  *G01R 27/08*   (2006.01)
  *G01R 31/08*   (2006.01)
  *G01N 27/00*   (2006.01)

(52) U.S. Cl. .................... 324/700; 324/71.2; 324/527

(58) Field of Classification Search .............. 324/527, 324/512, 500, 228, 627, 557, 718, 456, 216, 324/217, 240, 229, 700, 716, 71.2, 71.1, 324/76.11, 237, 238; 205/775, 791, 790.5
See application file for complete search history.

(56) References Cited

U.S. PATENT DOCUMENTS

| | | | |
|---|---|---|---|
| 3,745,452 A | 7/1973 | Osburn et al. | |
| 4,064,452 A | 12/1977 | Toth | |
| 4,390,836 A | 6/1983 | Bruce et al. | |
| 4,438,389 A | 3/1984 | De Sa | |
| 4,504,365 A | 3/1985 | Kellner | |
| 4,970,467 A | 11/1990 | Burnett | |
| 5,087,873 A | 2/1992 | Murphy et al. | |
| 5,120,381 A | 6/1992 | Nee | |
| 5,126,654 A | 6/1992 | Murphy et al. | |
| 5,584,978 A | 12/1996 | Van Blaricom | |
| 5,828,219 A | 10/1998 | Hanlon et al. | |
| 6,051,977 A | 4/2000 | Masuda et al. | |
| 6,127,827 A | 10/2000 | Lewis | |
| 6,388,431 B1 | 5/2002 | Kramer et al. | |
| 7,356,421 B2 * | 4/2008 | Gudmundsson et al. | 702/38 |
| 7,414,395 B2 * | 8/2008 | Gao et al. | 324/220 |

(Continued)

OTHER PUBLICATIONS

International Search Report and Written Opinion mailed on Mar. 10, 2010 by the ISA/US Office in counterpart application No. PCT/US2009/005937.

(Continued)

*Primary Examiner*—Hoai-An D Nguyen
(74) *Attorney, Agent, or Firm*—Abelman, Frayne & Schwab

(57) ABSTRACT

Method and apparatus for simulating electrical pipe-to-soil impedance of a coated segment of a pipeline includes simulating a current injection point to a buried pipe section, simulating a first output signal from a magnetometer positioned at a first location over the buried pipe section, simulating a second output signal from a magnetometer positioned at a second location over the buried pipe section, simulating bonding of pipe coating of the pipe section, and simulating soil resistance of a soil environment surrounding the buried pipe section. The invention includes both field-test simulation with calibration pipe samples, and bench-test simulation using electronic simulation of the pipe coating. The simulations may be used for test and general calibration of MEIS pipeline coating inspection systems.

8 Claims, 19 Drawing Sheets

U.S. PATENT DOCUMENTS

| | | | |
|---|---|---|---|
| 2002/0193977 A1* | 12/2002 | Elco | 703/15 |
| 2003/0169058 A1* | 9/2003 | Pierre et al. | 324/700 |
| 2003/0211310 A1 | 11/2003 | Haas et al. | |
| 2006/0144721 A1 | 7/2006 | Bonitz et al. | |

OTHER PUBLICATIONS

"Evaluation of Organic Coatings with Electrochemical Impedance Spectroscopy", Loveday, Peterson and Rodgers, *JCT Coatings Tech*, Part 2, pp. 88-93, Oct. 2004.

"Evaluation of Organic Coatings with Electrochemical Impedance Spectroscopy", Loveday, Peterson and Rodgers, *JCT Coatings Tech*, Part 1, pp. 46-52, Aug. 2004.

"Gap Analysis of Location Techniques for CP Shielding", Brossia, Song and Sridhar, *PRCI.com Publications*, pp. 1-2 (Abstract), Publ. L52131e, Jul. 1, 2004.

"Pipeline Current Mapper User Guide", Rev. 7, Radiodetection Corp., Apr. 11, 2002.

"The Study of Detection Technology and Instrument of Buried Pipeline-Coating Defaults", Shinjiu, et al., *Proceedings of the 4th World Congress on Intelligent Control and Automation*, Institute of Electrical and Electronic Engineers, pp. 794-798, Jun. 10-14, 2002.

"Electrochemical Impedance of Coated Metal Undergoing Loss of Adhesion", Sculley, Silverman, Kendig, *Electromechanical Impedance: Analysis and Interpretation*, ASTM STP 1188, American Society for Testing and Materials, pp. 407-427, 1993.

"Crude Oil Pipeline Rupture," *Pipeline Investigation Report P99H0021*, Transportation Safety Board of Canada, Mar. 2002.

"Corrosion Detection on Underground Gas Pipeline by Magnetically Assisted AC Impedance", Srinivasan, Murphy, Schroebel and Lillard, *Materials Performance*, vol. 30, No. 3, NACE, pp. 14-18, Mar. 1991.

"Magnetic Field Measurement of Corrosion Processes", Murphy, Hartong, Cohn, Moran, Bundy and Scully, *Journal of the Electrochemical Society*, vol. 135, No. 2, pp. 310-313, Feb. 1988.

* cited by examiner

METHOD AND APPARATUS FOR SIMULATING ELECTRICAL CHARACTERISTICS OF A COATED SEGMENT OF A PIPELINE

CROSS-REFERENCE TO RELATED APPLICATIONS

This application contains subject matter related to commonly assigned U.S. application Ser. No. 12/291,528 and application Ser. No. 12/291,530, both of which being co-filed contemporaneously herewith and the contents of which are incorporated by reference herein in their entireties.

BACKGROUND OF THE INVENTION

1. Field of Invention

This invention relates generally to methods and apparatus for averting corrosion of pipelines, and more specifically, the present invention relates to optimizing the detection and location of defects in coatings on the pipe structures without the necessity of excavation or local physical contact with the pipe.

2. Description of the Prior Art

Pipelines that are used to transport fluids, such as petroleum or other types of fluids or gases are often buried beneath the ground to preserve the above-ground real estate for other uses, as well as to protect the pipelines from the environment. The piping used to form the pipelines is coated to prevent corrosion. In fact, the coating integrity of the buried pipes is crucial to the prevention of outside surface (i.e., outside diameter (OD)) corrosion.

A disbonded coating defeats the security provided by cathodic protection on the pipe. The cathodic protection currents can no longer flow out through the coating to the cover soil as intended. Disbonds that are not repaired can lead to moisture ingression between the coating and the outer surface of the pipe, which can eventually result in corrosion and/or stress-corrosion cracking of the pipe. For a detailed understanding the effects of disbonds in pipeline coatings the reader is directed to the article *Crude Oil Pipeline Rupture*, Pipeline Investigation Report P99H0021, Transportation Safety Board of Canada, March 2002, the content of which is incorporated by reference herein in its entirety.

Corroded surfaces and stress-corrosion cracking along the pipe are much more costly to repair than simply repairing an area of the pipe having a coating that is disbanded. As a result, early detection of pipeline coating disbonds is necessary to maintain the integrity of a pipeline.

The detection and characterization of disbanded and/or defective coating using EIS (Electrochemical Impedance Spectroscopy) is well known. For example, the article entitled "Evaluation of Organic Coatings with Electrochemical Impedance Spectroscopy" by Loveday, et al., JCT Coatings Tech, October 2004, pp. 88-93 describes the general application of EIS to coatings. Moreover, an article entitled "Electrochemical Impedance of Coated Metal Undergoing Loss of Adhesion", by Kendig, Martin W., et al, *Electrochemical Impedance: Analysis and Interpretation*, ASTM STP 1188, Scully, Silverman, and Kendig, eds., American Society for Testing and Materials, 1993, pp. 407-427 describes EIS responses to various coating conditions, including normal coating, coating at the onset of corrosion and disbonded coating. The contents of both of these articles are incorporated by reference herein in their entirety.

The basic procedure is to measure the complex electrical impedance through the metal-to-coating interface at multiple frequencies followed by analysis of the impedance data. Displaying the data on Nyquist and Bode plots can reveal substantial information about the properties of the coating. Commercial software is available for fitting Nyquist-plot data to operator-selected equivalent circuits of the coating interface. The values of the resulting circuit components can reveal direct information on coating properties.

Application of EIS to pipeline coating inspection has been reported in an article entitled "The Study of Detection Technology and Instrument of Buried Pipeline Coating Defects", by Shijiu, et al., *Proceedings of the 4$^{th}$ World Congress on Intelligent Control and Automation*, Institute of Electrical and Electronic Engineers, 2001, pp. 794-98, the content of which is incorporated by reference herein in its entirety. This article describes the ability to determine coating quality and type of defect using the measured EIS spectrum of the coating, as well as to differentiate between coating defects and coating disbonds using the EIS data.

EIS requires direct contact with the coating surface, necessitating excavation of the pipes, which can be burdensome and costly to perform. In an article by Murphy, J. C., et al., entitled "Magnetic Field Measurement of Corrosion Processes", *Journal of the Electrochemical Society*, Vol. 135, No. 2, February 1988, pp. 310-313, it is disclosed that this problem of having to first excavate the pipes has been circumvented by the development of MEIS (Magnetically-detected Electrochemical Impedance Spectroscopy), the content of which is incorporated by reference herein in its entirety.

MEIS uses above-ground magnetometers to measure on-pipe current resulting from applying an AC voltage between the pipe and a remote ground-return electrode. A reference electrode is placed on the soil adjacent to the pipe. The actual pipe-to-soil voltage can be measured via this electrode independently of the effects of earthing resistance of the ground-return electrode.

The pipe-to-soil impedance of a segment of pipe can be determined by measuring the on-pipe current via a magnetometer sequentially positioned at two locations defining the ends of the segment, followed by calculating the differential net AC impedance of the segment. The pipe-to-reference electrode voltage is utilized along with the on-pipe current for these calculations. This procedure is described in the above-identified Murphy article which discloses: a) MEIS-measured Bode and Nyquist plots for each end of a pipe segment; and b) the resultant Bode and Nyquist plots for the segment itself. This procedure is also described in an article by Srinivasan, R. et al., entitled "Corrosion Detection on Underground Gas Pipeline by Magnetically Assisted AC Impedance", *Materials Performance*, vol. 30, no. 3, NACE, Houston, Tex., 1991, pp. 14-18, the contents of which are incorporated by reference herein in their entirety.

Standard EIS analysis techniques can be then be applied to the pipe-segment's impedance. The equivalent circuit of the segment's pipe-to-soil interface can be determined via conventional analysis of Bode and Nyquist plots of this impedance data. This analysis can utilize a Randles equivalent circuit or other equivalent circuit of the coating interface. The component values of the equivalent circuit can be analyzed to determine integrity of the coating, including degree of disbond or damage, as reported in the above mentioned articles by Kendig, et al. and Shijiu, et al. For additional information describing the use of MEIS technology for determining corrosion rate measurements, the reader is directed to U.S. Pat. No. 5,126,654 to Murphy et al., the content of which is also incorporated by reference herein in its entirety. The Murphy patent describes the use of MEIS to calculate the resistance and capacitance of the pipe-to-soil interface, and using these values to characterize the corrosion rate.

A. General Background of MEIS Apparatus

One configuration of a pipe coating inspection system includes a Pipe Scanner Subsystem and a Magnetically-detected Electrochemical Impedance Spectroscopy (MEIS) Subsystem. This system can be used to periodically test for pipeline faults and coating disbonds.

The Pipe Scanner Subsystem is intended for rapid screening of pipelines. It has the potential to identify areas where injected current is exiting the pipe in an abnormal manner, indicating a possible compromised or unbonded coating.

The MEIS Subsystem can then be used to further characterize the suspect area. As further used herein, "MEIS" is an abbreviation for Magnetic Electrochemical Impedance Spectroscopy. It is an extension of an EIS (Electrochemical Impedance Spectroscopy) procedure, which characterizes corrosion by direct electrical contact with the corrosion site. In contrast to EIS, MEIS performs remote measurements using a magnetometer to detect current flow in the test object, e.g., section of pipe under test. MEIS characterizes the coating by multi-frequency analysis of the complex electrical impedance between the pipe and soil. The results can be plotted on a Nyquist plot to characterize disbonds, holidays and/or microcracks in the pipe coating.

Pipe scanning activity consists of data acquisition, namely, a field operator walking along the pipeline and recording on-pipe current. This can be augmented by also recording GPS location and time for each measurement point using a system data collector, and then analyzing this data with a Geographical Information System (GIS). For data acquisition, the operator can be equipped with a commercially available pipeline current mapper (PCM), a Global Positioning System (GPS) receiver, and a data collector, which includes specialized software suitable for this application.

Data can be uploaded from the data collector to a system computer for analysis. The system computer includes a pipeline data analysis program which can generate a graphical user interface (GUI) that exhibits the data on the display panel for inspection. However, the prior graphical user interfaces do not feature a combined display of a digitally-referenced map of the scanning area with data locations overlaid on the map, a pipeline current plot, and several lines of data in a spreadsheet format under the plot, wherein these displays are linked, so that the selected location is highlighted in all three views on the GUI. Accordingly, there is a need for a graphical user interface to enable a user to examine the pipeline current plot for indications of coating anomalies, such that initial decisions on coating quality and locations for subsequent MEIS testing can be made based on identifying areas where the on-pipe current deviates from its normal rate of exponential decay with distance from the transmitter.

The results of the MEIS subsystem responses vary depending on the particular soil environments in which the pipes are buried. In order to enhance a field test operator's ability to comprehend the results of the testing plotted on a Nyquist plot, it is desirable to enable the test operator to simulate various coating conditions in a laboratory or bench environment prior to conducting the actual testing in the field. Therefore, there is a need for a bench test simulator for simulating various types of disbonds while in the laboratory. There is also a need for a field test simulator for simulating various types of disbonds while in the field.

It has been observed that some pipes can carry substantial amounts of power line ground-return current. In some cases, the 60 Hz signal component in the magnetometer output can overdrive the MEIS system input, or can mask the much lower level of MEIS current.

One solution includes stop-band filtering at 60 Hz. However, this technique is not highly practical for the MEIS subsystem because the filter will interfere with other MEIS test frequencies in proximity to 60 Hz. Another solution is digital signal processing such as a Fast Fourier Transform (FFT), after which the offending signal components can be deleted. However, this requires an input dynamic range large enough to acquire a large 60 Hz interfering signal, while still having adequate resolution for the small MEIS signal. This is not practical with certain potentiostat circuitry used for MEIS. Therefore, there is a need for an improved method and apparatus to suppress the unwanted signal to overcome the disadvantages of the 60 Hz power line signals.

It has been further observed that soils with subsurface saltwater can adversely alter the measurements of the MEIS subsystem in terms of both attenuation and phase shift between the injection point (End-1) and the next cathodic protection (CP) test point or pipe access point (End-2). This indicates that the voltage may obey a complex propagation constant similar to that which would be encountered on an electric transmission line. This also means that standard MEIS may be impractical in these types of soil conditions because the pipe voltage at the test segment location can not be inferred by measuring the voltage at remote CP test points or other pipe access points. Accordingly, there is a need to provide an alternative approach to estimate the voltage at the MEIS test segment location.

SUMMARY OF THE INVENTION

The present invention incorporates several improvements to MEIS for practical application in the field. These improvements include: (a) methods for fabricating calibration pipes with simulated coating disbond to produce a field-test pipeline simulator; and (b) a bench-test pipeline simulator for performing laboratory calibration of MEIS systems.

Field Test Simulator

In one aspect of the present invention, a method is provided for fabricating pipeline coating samples containing synthetic disbonds to be used in estimating a condition of a coating of an underground pipeline. The method includes the steps of providing a section of a pipe having a predetermined diameter and length, installing end caps on opposing ends of the pipe section, where each end cap has an electrical connection extending therefrom, applying a material having a low dielectric coefficient around the pipe segment between the end caps to simulate an air-filled disbond, varying the coverage area of material to simulate various disbond sizes, and wrapping the pipe segment and end caps with tape to cover the material having a low dielectric coefficient.

In one embodiment, the pipe segment is coated with a primer prior to applying the material having a low dielectric coefficient around the pipe segment. In one embodiment, the material of low dielectric coefficient has a dielectric coefficient approximate to that of air. In one embodiment, the material of low dielectric coefficient is closed-cell sponge rubber sheeting.

Bench Test Simulator

In another aspect of the present invention, a method is provided for field calibration of the MEIS system using buried coated pipe samples containing synthetic disbonds. The pipeline coating samples include a section of pipe having a predetermined diameter and length, an end cap disposed over each end of the pipe section, a low dielectric material wrapped around the pipe section between the end caps to simulate various sizes of disbonds, and a sealing tape wrapped over the low dielectric material, the balance of the pipe, and end caps. The method includes the steps of burying the pipe section in the soil at a predetermined depth, applying a voltage at varying frequencies between the pipe and a ground-return electrode, and measuring input and output currents from the sample pipe. The equivalent complex impedances at input and output locations along the sample pipe are computed and can be stored for future reference. The net pipe-to-soil impedance of the test pipe can be calculated from this data. This impedance may be analyzed using conventional EIS techniques to determine the measurement capability of the MEIS system.

In yet another aspect of the present invention, a pipeline simulator is provided for simulating electrical pipe-to-soil impedance of a coated segment of a pipeline. The pipeline simulator includes a current injection point for providing current to a first test point representing an up-pipe location along the segment of pipeline, where a first magnetometer measurement is taken between the up-pipe location and ground, and a leakage current circuit is electrically coupled to the current injection point and ground. The leakage current circuit can include a standard Randles circuit to simulate pipe-to-soil impedance of a pipe segment. In one embodiment, the resistive elements simulating both the coating resistance and the soil resistance (earthing resistance of the simulated pipe segment) are selectable by an operator and have values simulating various bond conditions of the coated segment of the pipeline.

A second test point representing a down-pipe location along the segment of pipeline is provided to simulate where a second magnetometer measurement is taken between the pipeline segment and ground.

In one embodiment, the simulated coating resistance in the Randles circuit includes a resistor, an open circuit and a short circuit, selectable by a switch, wherein the resistor represents a normal bond between the pipeline and the coating, the open circuit represents a disbond between the pipeline and the coating, and the short circuit represents a holiday between the pipeline and the coating. A plurality of switch-selectable resistive values, including an open circuit, may be used for the simulated earthing resistance In one embodiment, the first test point includes a current-sensing resistor coupled between the injection point and the leakage current circuit, and a first op amp having first and second inputs respectively coupled to first and second ends of the sensing resistor, and an output forming the first test point, wherein a voltage at the output is proportional to the current provided at the current injection point.

In another aspect of the present invention, an apparatus for simulating electrical pipe-to-soil impedance of a coated segment of a pipeline includes means for simulating a current injection point to a buried pipe section, means for simulating a first output signal from a magnetometer positioned at a first location over the buried pipe section, means for simulating a second output signal from a magnetometer positioned at a second location over the buried pipe section, means for simulating various pipe-to-soil impedances for the pipe section, and means for simulating soil or earthing resistance of a soil environment surrounding the buried pipe section.

In still another aspect of the present invention, a method for simulating electrical pipe-to-soil impedance of a coated segment of a pipeline includes simulating a current injection point to a buried pipe section, simulating a first output signal from a magnetometer positioned at a first location over the buried pipe section, simulating a second output signal from a magnetometer positioned at a second location over the buried pipe section, simulating various pipe-to-soil impedances for the pipe section, and simulating soil or earthing resistance of a soil environment surrounding the buried pipe section.

These and other objects, features and advantages of the present invention will be apparent from the following detailed description of the preferred embodiments taken in conjunction with the attached drawings, wherein like reference numerals denote like or similar elements.

DETAILED DESCRIPTION OF THE PREFERRED EMBODIMENTS

An advantageous function of a pipeline coating inspection system is the ability to estimate the condition of the pipe coating at selected locations of the pipe. The estimates can be provided using well-known MEIS techniques to measure the net complex impedance of the pipe-to-soil junction for a segment of pipe, such as described in the aforementioned Murphy and Srinivasan references. The impedance is measured over a range of frequencies, and the results can be plotted on graphical displays such as Nyquist or Bode plots. Alternatively, the complex admittance of the data (inverse of impedance) can be plotted. Analysis of the plots using long-established EIS methods can be used to potentially reveal the following coating properties: normal bonds, disbonds (with potential differentiation between air-filled, water-filled, and corrosion product in the disbond area), holidays and microcracking. Although the present invention is described herein as being used to estimate the condition of a pipeline coating, a person of ordinary skill in the art will appreciate that the present invention is also applicable to other buried metal structures having a coating that is subject to corrosion or deterioration caused by its environment.

Figure 1:
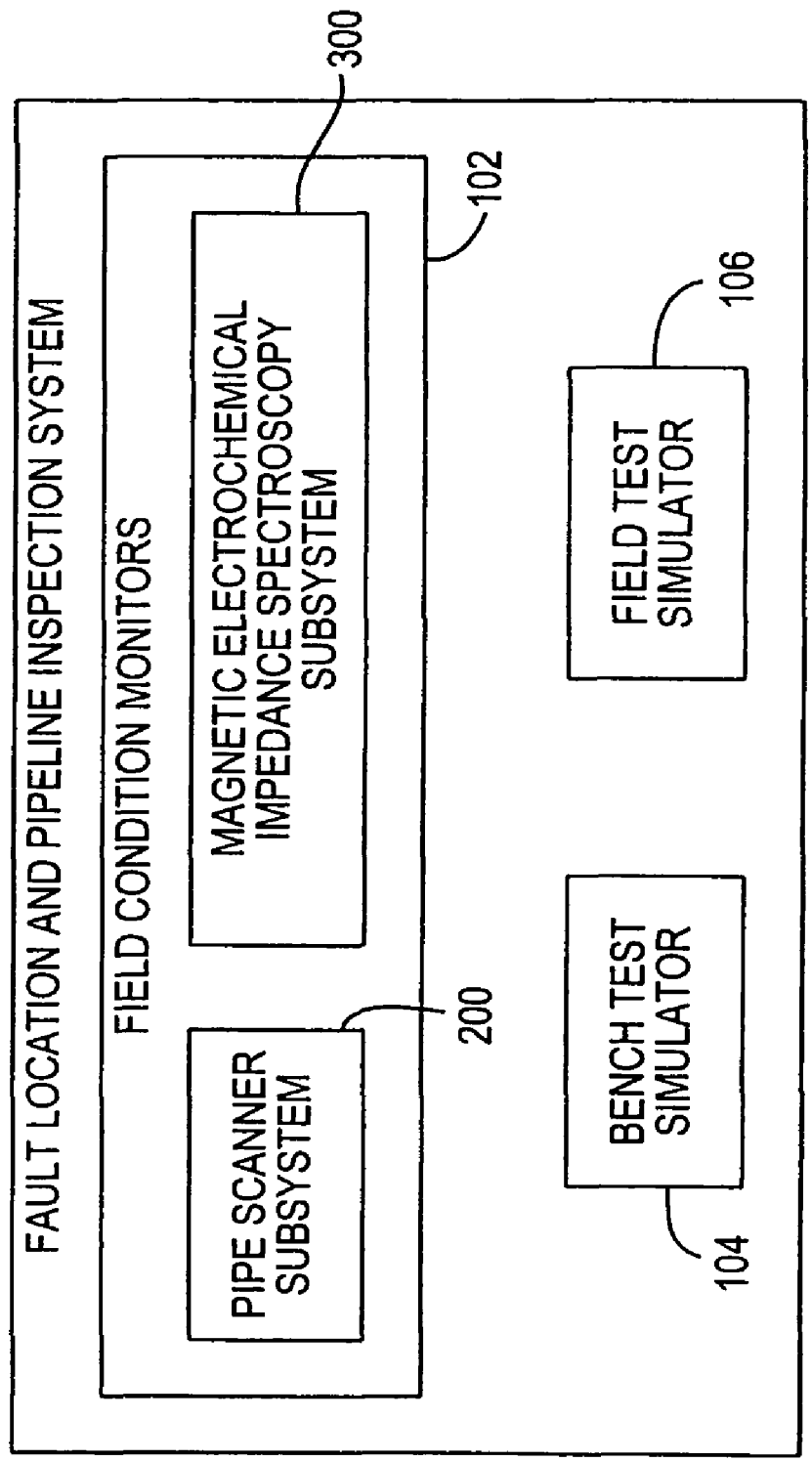
FIG. 1 is a functional block diagram of a fault location and pipeline inspection system including field condition monitors, a bench test simulator and a field test simulator in accordance with the present invention.

Referring to FIG. 1, the pipeline inspection system 100 of the present invention includes a field condition monitor 102, a bench test simulator 104, and field test simulators 106. The simulators 104 and 106 can be used to calibrate and/or test the MEIS system in both the laboratory and the field. That is, the simulators 104 and 106 enable a test operator to set up parameters that are seen in the field and observe the results to improve actual detection of coating defects.

Figure 2:
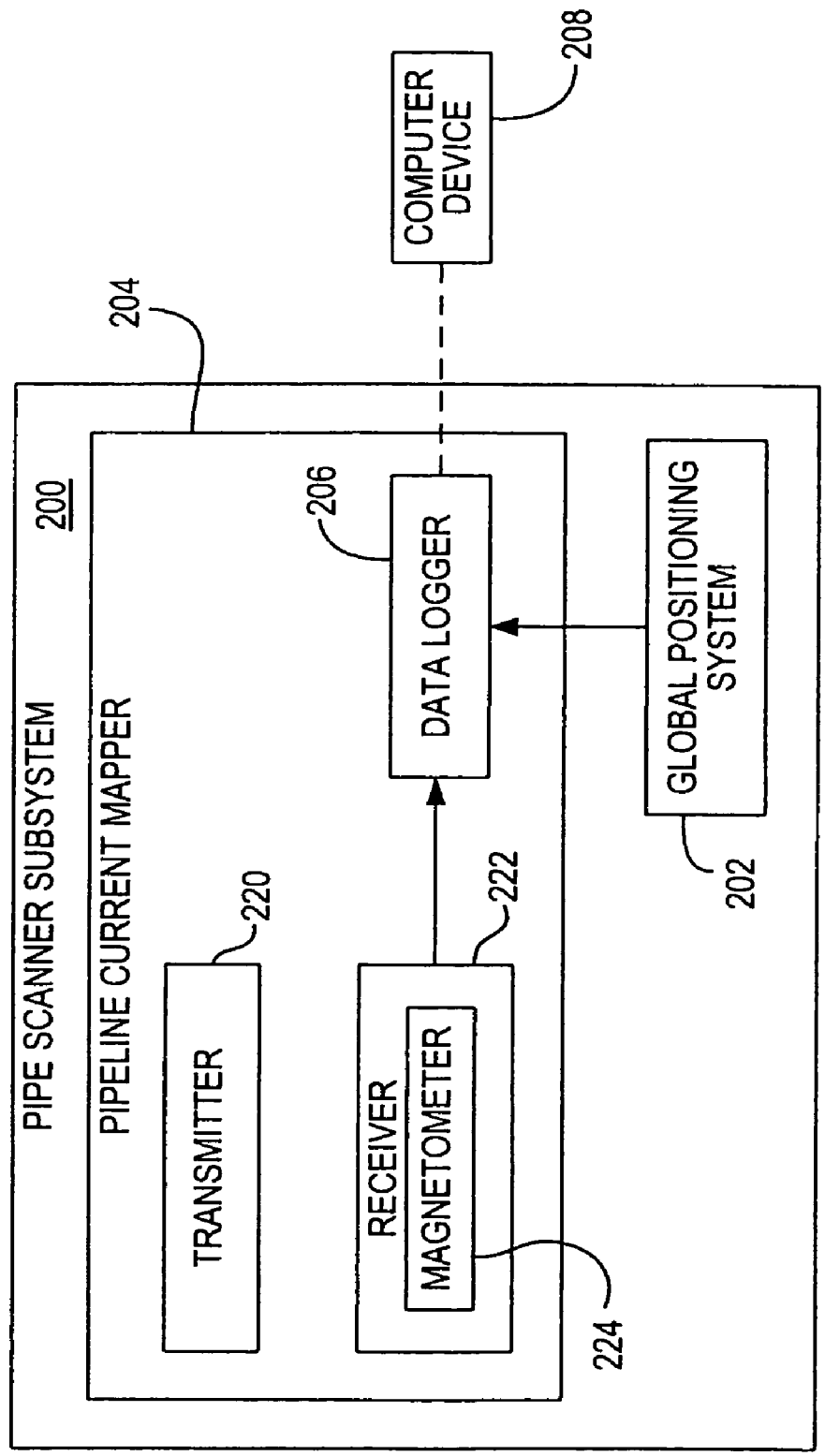
FIG. 2 is a block diagram of a pipe scanner subsystem of the field condition monitors of the system of FIG. 1.
Figure 3:
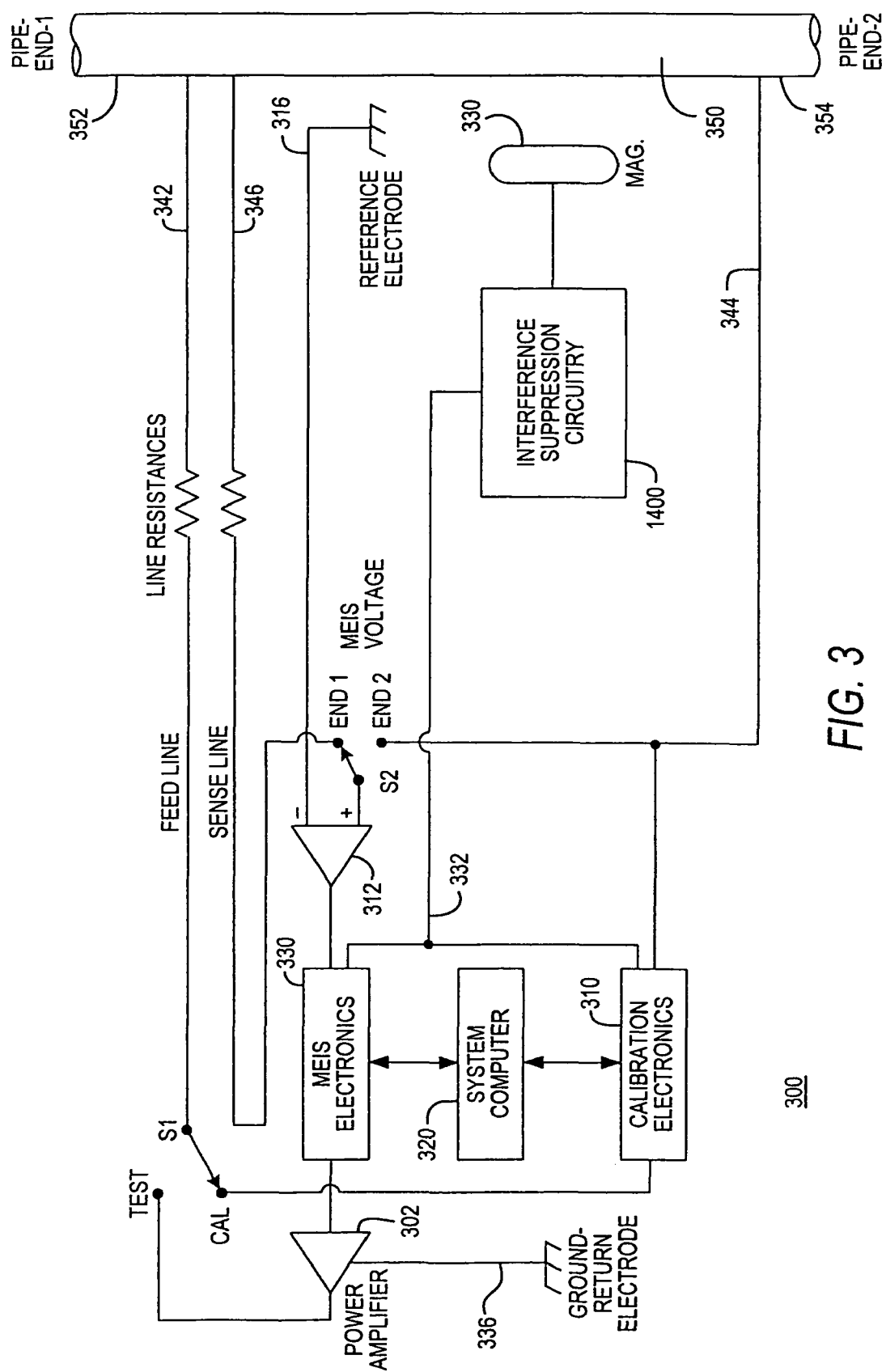
FIG. 3 is a schematic view of a magnetic electrochemical impedance spectroscopy (MEIS) subsystem of the field condition monitors of the system of FIG. 1.

The field condition monitor 102 includes a pipe scanner subsystem 200 and a magnetic electrochemical impedance spectroscopy (MEIS) subsystem 300 respectively illustrated in FIGS. 2 and 3. The Pipe Scanner Subsystem 200 is used for rapid screening of pipelines, and has the potential to identify areas where current is exiting the pipe in an abnormal manner, indicating possible compromised or disbonded coating. The MEIS Subsystem 300 is used to further characterize the suspect area as, for example, a disbond (e.g., air filled or moisture filled disbond) a holiday or micro-cracking of the pipeline coating. The MEIS subsystem 300 characterizes the coating by multi-frequency analysis of the complex electrical impedance between the pipe and soil.

Pipe Scanner Subsystem

Referring to FIG. 2, the Pipe Scanner Subsystem 200 includes a Global Positioning System (GPS) receiver 202, a Pipeline Current Mapper (PCM) 204, a computerized data logger (collector) 206, and an optional computer device 208, such as a laptop computer or other computer device having a conventional display panel. The GPS receiver 202 and PCM 204 are coupled to input ports of the data collector 206. The optional computer device 208 is coupled to a port of the data collector 206 for uploading of post-test data.

The GPS receiver 202 can be any well-known GPS system, such as a TRIMBLE GPS PATHFINDER™ manufactured by Trimble Navigation Limited of Sunnyvale, Calif., USA. The PCM 204 can be any well-known pipeline current mapper, such as a PCMPLUS+ manufactured by Radiodetection Ltd, of Bristol, UK. The data collector 206 can be any well-known data collector, such as a RANGER data collector produced by TRIPOD DATA SYSTEMS of Corvallis Oreg., USA. It is noted that a person of ordinary skill in the art will appreciate that other equipment manufacturers of the GPS receiver, pipeline current mapper and data collector can also be utilized to provide current and geographical measurements of the pipeline.

The data collector 206 can be a hand-held computer device with one or more input ports, allowing it to simultaneously connect to the PCM and the GPS systems. Alternatively, a combination hand-held computer with integral GPS features, such as the TRIMBLE GEOXT manufactured by Trimble Navigation Limited of Sunnyvale, Calif., USA, can be utilized. In one embodiment, the data collector 206 includes a WINDOWS® type operating system, such as WINDOWS CE®, although such operating system is not considered limiting. The data collector 206 further includes a display panel, at least one output port, a control panel (e.g., keyboard and function buttons), and an application program (e.g., PIPES-CAN) stored in memory thereof for collecting and displaying location information from the GPS receiver 202 and other data.

The pipeline current mapper 204 includes a transmitter, receiver and a magnetometer that are used for measuring injected on-pipe current from the buried pipeline. During pipe scanning operations, the pipe is electrically driven with the transmitter of the PCM system 204. The transmitter is temporarily connected in place of the nearest cathodic protection rectifier or can be connected between any cathodic protection test point on the pipe and a suitable ground-return electrode (e.g., ground rod). In one embodiment, all three test frequencies available in the commercial PCM can be utilized, which include 4 Hz for on-pipe current and pipe depth readings; 8 Hz which is used in conjunction with 4 Hz data for determining current direction; and a locator frequency which is used to find the pipe and to center the PCM over the pipe prior to taking readings. In one embodiment, the locator frequency can be selected at 512 Hz or 135 Hz. The pipe scanning activity is conducted using only two frequencies, preferably 4 Hz and 135 Hz, to maximize the allowable distance between the system and the transmitter.

The PCM receiver is preferably a portable receiver used to both locate the buried pipeline and measure on-pipe current. The receiver provides the operator with measurement of pipe depth, as well as strength and direction of the current injected by the system's transmitter. The receiver's internal magnetometers detect all on-pipe current. When a PCM measurement is taken, the data collector 206 stores a unique identification (e.g., log) number associated with the current as measured in milliamps and dB, current direction, as well as depth of the pipeline (illustratively measured in centimeters). In this manner, as the field operator walks along the pipeline, the data collector 206 is used to save the PCM measurements at each test location.

During the data analysis phase, the measured data can be uploaded from the data collector 206 to the system computer 208 via a serial or USB port for analysis. The computer device 208 includes a pipeline data analysis program 230 (FIG. 4), such as the PIPELINE EXPLORER program produced by HD Laboratories of Issaquah, Wash., USA, which acquires the data from the data collector 206 and displays it for inspection. In one embodiment of the present invention, the data is displayed as a graphical user interface (GUI), as shown below with respect to FIG. 5.

Figure 4:
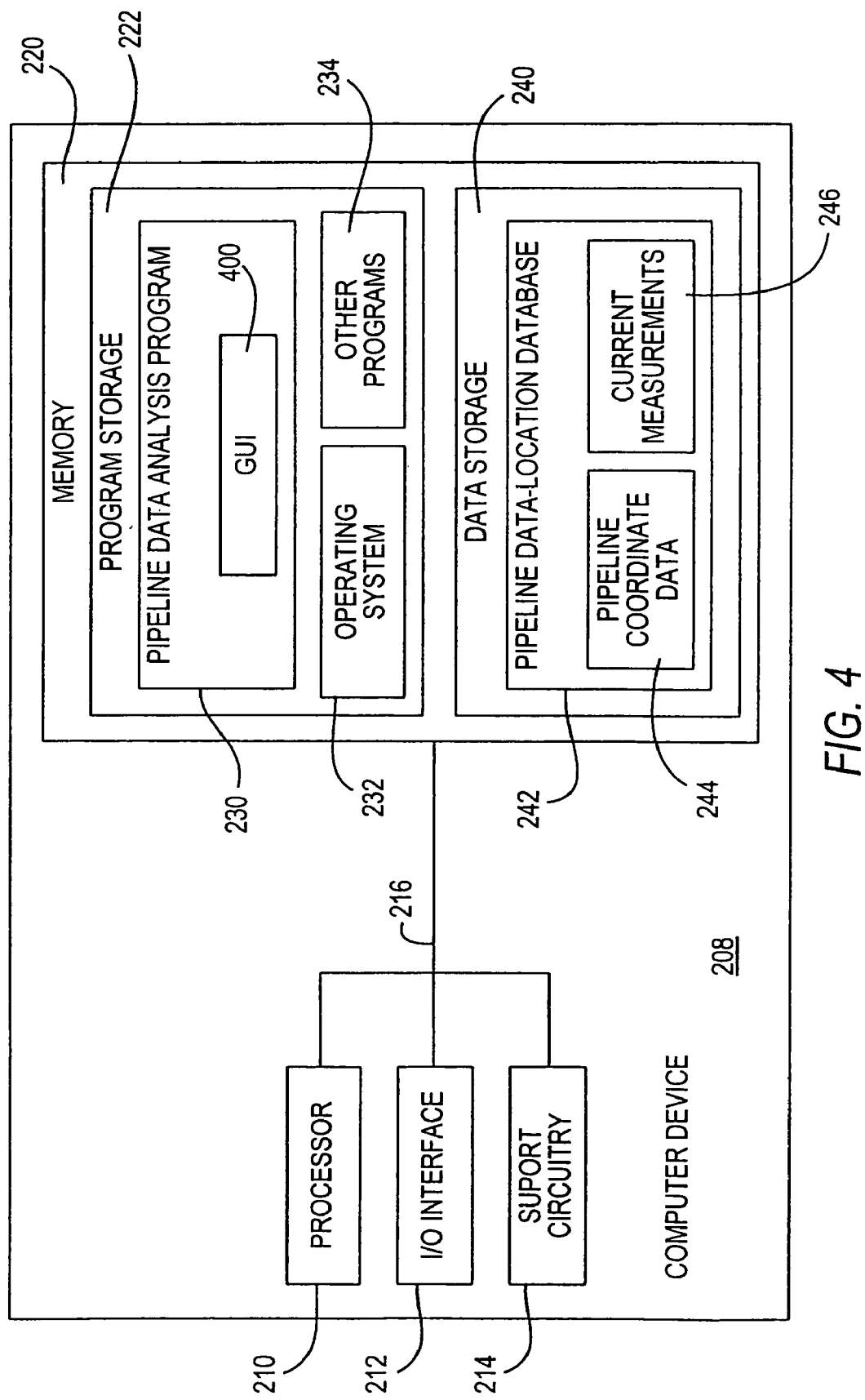
FIG. 4 is a block diagram of a computer device of the pipe scanner subsystem of FIG. 2.

Referring now to FIG. 4, the computer device 208 can be any computer device such as a personal computer, minicomputer, workstation or mainframe, or a combination thereof. Preferably, the computer device 208 is a portable computer device, such as a laptop or other handheld computer device.

Specifically, the computer device 208 comprises at least one processor 210, as well as memory 220 for storing various programs and data.

The processor 210 can be any conventional processor, such as one or more INTEL® Processors. The memory 220 can comprise volatile memory (e.g., DRAM), non-volatile memory (e.g., disk drives) and/or a combination thereof. The processor 210 also cooperates with support circuitry 214, such as power supplies, clock circuits, cache memory, among other conventional support circuitry, to assist in executing software routines (e.g., the programs for generating GUI 500 (FIG. 5)) stored in the memory 220 in a known manner. The one or more processors 210, memory 220 and support circuitry 214 are all commonly connected to each other through one or more bus and/or communication mediums (e.g., cabling) 216.

The computer device 208 also comprises input/output (I/O) circuitry 212 that forms an interface between various functional elements communicating with the computer device 208. For example, the computer device 208 is connected to the data collector 206 through an I/O interface 212, through which information can be transferred therebetween.

The memory 220 includes program storage 222 and data storage 240. The program storage 222 stores a pipeline data analysis module 230 of the present invention, an operating system 232, such as a WINDOWS® operating system, among other application programs and data retrieval modules 234. The data storage 240 can be an internal or separate storage device, such as one or more disk drive arrays that can be accessed via the I/O interface 212 to read/write data. It is noted that any of the software program modules stored in the program storage 222 and data stored the data storage 240 are transferred to specific memory locations (e.g., RAM) as needed for execution by the processor 210.

The data storage 240 includes a pipeline data-location database 242 that stores pipeline coordinate data 244 and current measurements 246 for each test location taken by the PCM along the pipeline in accordance with the present invention, among other information uploaded from the data collector 206. In particular, pipeline coordinate information is provided to the data collector 206 from the GPS receiver 202. The data collector 206 saves the coordinate information, for example, as a table or spreadsheet file that includes latitudinal and longitudinal information of the pipeline. The coordinate information from the data collector 206 can be uploaded in its present form or converted prior to or after storage in the memory 220 of the computer device 208.

It is further contemplated that some of the process steps discussed herein as software processes may be implemented within hardware, for example, as circuitry that cooperates with the processor 210 to perform various steps. It is noted that the operating system 232 and optionally various application programs are stored in the memory 220 to run specific tasks and enable user interaction. It is further noted that the computer device shown and described with respect to FIG. 4 is provided for illustrative purposes only and similar computer devices can be used for storing and executing any of the programs and data described herein.

Figure 5:
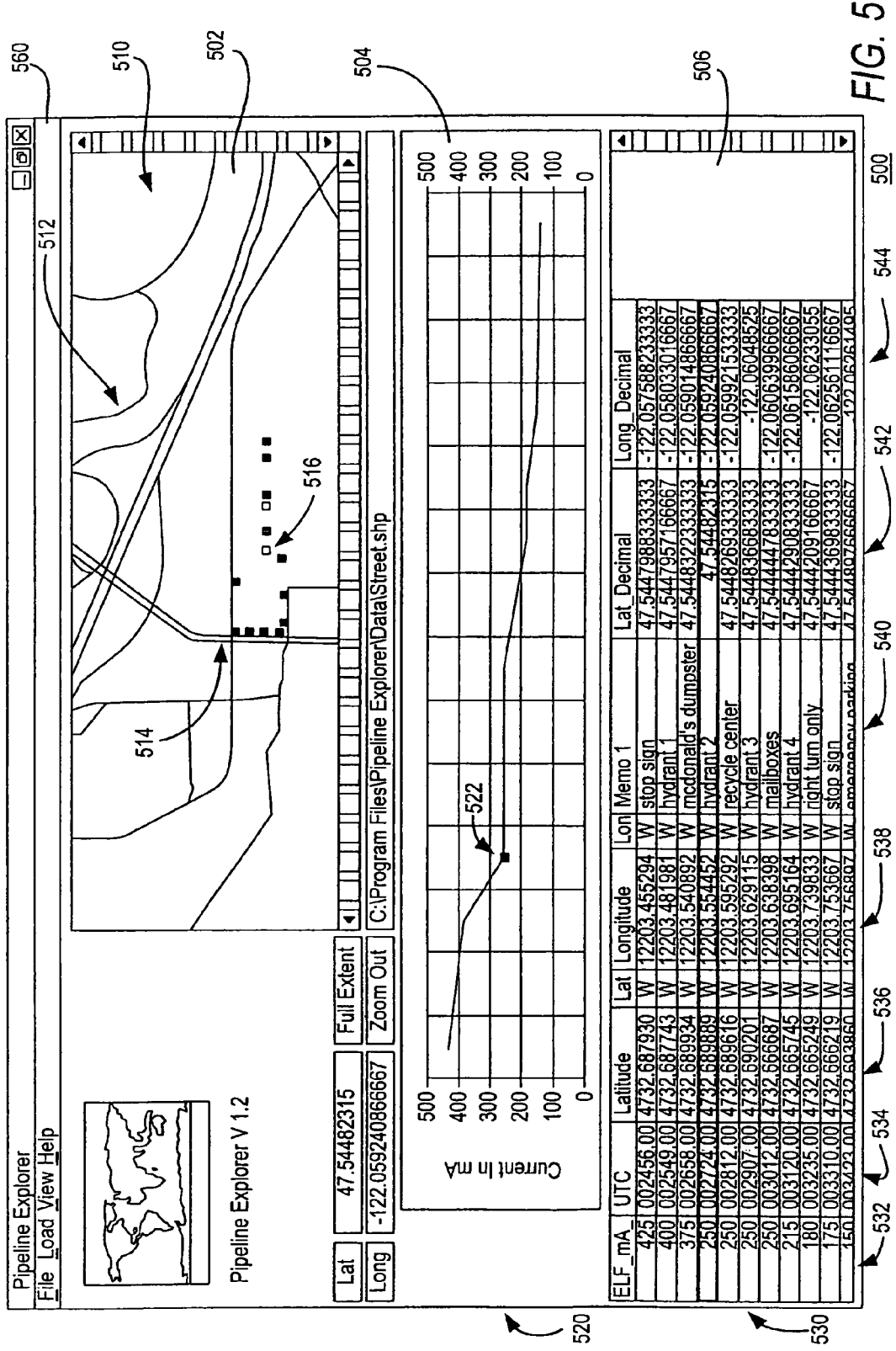
FIG. 5 is a graphical representation of a graphical user interface (GUI) of the pipe scanner subsystem of FIG. 2.

Referring now to FIG. 5, a graphical representation of a graphical user interface (GUI) of a geographic information system (GIS) for analyzing pipeline current data on the computer device 208 is shown. In one embodiment of the present invention, the GIS display 500 of the data analysis program can be a WINDOWS® style GUI that highlights data points taken during field operations by the pipe scanner subsystem 200. The data points are tracked and displayed, illustratively, in three windows including a first (e.g., upper) window portion 502, a second (e.g., middle) window portion 504, and a third (e.g., lower) window portion 506.

Each window portion can include a scroll bar or other navigational icon/tool for navigating and displaying additional information within the window portion. The GUI 500 can also include a tool bar 560 and/or pull down menu for selecting one instance of data from a set of instances of data, such as measurement points along the pipeline.

In one embodiment, the GUI 500 includes a tool bar 560 that enables the user to create and save a file, such as a spread sheet type file (e.g., MS EXCEL file), as well as load data, enhance the view being displayed, provide additional help, among other features. Additional buttons can be provided to allow a user to zoom-in or zoom out the present view on the display panel.

The first window 502 of the GUI illustratively displays a digital map 510 of the pipeline scanning area 512 that plots the GPS location of measurement points i.e., data locations 514 overlaid on the map 510. The second window 504 illustratively displays a pipeline current plot 520. That is, the second window 504 displays the on-pipe current generated by the PCM transmitter. The third window 506 illustratively displays several lines of data in a spreadsheet format 530 under the plot 520.

In one embodiment, the display is Read-Only, but the GUI enables a user to highlight various attributes within the various windows. For example, the user can highlight a location point on the digital map 510, a data point on the current plot 520, and a data line in the table 530.

During execution of the pipeline data analysis program 230, the GPS pipeline coordinate data 244 and current measurements 246 stored in the pipeline data-location database 242 are accessed from memory 220 in the computer device 208 to generate the data points and tables displayed by the GUI 500.

In one embodiment, the third window 506 displays a plurality of fields (i.e., columns) in spreadsheet form. The plurality of fields illustratively include a first field labeled "ELF_mA" for displaying extremely low frequency on-pipe current (e.g., measured in milliamps) 532 measured at each location; a coordinated universal time (UTC) field 534, which is the time standard based the Earth's angular rotation as opposed to the previous passage of seconds; GPS coordinates including the latitude coordinate 536 and longitude coordinate 538, as well as the latitude coordinate 542 and longitude coordinate 544 in decimal format, all of which are associated with the measurements taken at the data locations 514 overlaid on the digital map 510. The plurality of fields can also include at least one memo field 540 for providing even more specific location information, such as landmarks, local terrain information or other field operator notation that is associated with the pipeline measurements taken by the field test operator. A person of ordinary skill in the art will appreciate that the fields shown in the third window 506 are not considered as being limiting.

The first, second and third window displays are linked so that the presently selected data location is highlighted in all three windows. For example, as shown in FIG. 5, the fourth row in the spreadsheet 530 of the third window 506 is illustratively selected (highlighted) by the field operator by using a mouse, keyboard or other navigational tool. As a result of the user's selection, the pipeline data analysis program 230 will contemporaneously display the current plot 520 for the selected data location in the second window 504, as well as highlight the specific data location 514 (e.g., one of the black dots along the pipeline) on the digital map shown in the first window 502.

As shown in FIG. 5, the highlighted fourth row in the third window 506 displays a current of 250 ma in the ELF_mA column 532, which is illustratively highlighted as a data point 522 in the current plot 520. Further, the latitudinal and longitudinal coordinates where the 250 ma current leakage occurred is provided in columns 542 and 544 of the table 530, and such location is illustratively displayed at 516 in the digital map 510 of the first window 502. The program 400 enables the corresponding test data points in both the digital map 510 and current plot 520 to be highlighted in real time as the operator scrolls up or down along the results provided in the table 530 of the third window 506.

Data analysis includes detecting areas where the on-pipe current deviates from its normal rate of exponential decay with distance from the transmitter. This is facilitated by the on-screen current plot 520 in the second window 504. Other plots may be constructed from the data for more detailed scrutiny, such as current loss rate measured in dB/(unit distance). The availability of GPS coordinate data allows the distance between measurement points to be calculated for this analysis.

The general procedure is to examine the pipeline current plot for indications of coating anomalies. Initial decisions on coating quality and locations for subsequent MEIS testing can be made based on the following criteria:

A normal coating will have a smooth decrease of 4 Hz current with distance away from the transmitter. This indicates that the pipe-to-soil impedance is uniform and that a corresponding, uniform amount of current per-unit of distance is leaking off to the soil through the high impedance of the bonded coating.

A disbond containing air or dry corrosion product will generate current shielding, and will decrease the rate of current departure per-unit distance. This can reduce the slope of the current-distance curve, resulting in a more horizontal trace on the plot.

A disbond containing water or a coating section with micro-cracking may result in increased current departure per-unit distance. The coating is compromised either at the water ingress location or at the crack sites, resulting in reduced pipe-to-soil impedance. This may increase the negative slope of the plot, or may produce a small step function downward in the plot.

A holiday will produce a larger departure of current from the pipe, and may result in a large step downward in the current plot. The on-pipe current could potentially be reduced to zero at this point, depending upon the size of the holiday and the impedance of the soil.

For an example of an analysis of various PCM plots and patterns described above, the reader is directed to the literature entitled "Pipeline Current Mapper User Guide", Rev. 7, Apr. 11, 2002, by Radiodetection Corp, the content of which is incorporated by reference in its entirety. Moreover, for an understanding of current shielding by disbanded coatings, the reader is directed to the article entitled "Gap Analysis of Location Techniques for CP Shielding" by Brossia et al, available through PRCI (Pipeline Research Council International), Publication L52131e, July 2004, the content of which is incorporated by reference in its entirety.

The locations showing abnormal leakage currents that are identified by the pipe scanner subsystem 200 can be further analyzed by the MEIS subsystem 300 described below.

MEIS Subsystem

As noted above, the Magnetic Electrochemical Impedance Spectroscopy (MEIS) subsystem 300 characterizes the coating by multi-frequency analysis of the complex electrical impedance between the buried pipeline and soil. The results can be plotted on a Nyquist plot to potentially identify and characterize disbonds, holidays and/or micro-cracks in the pipe coating.

Referring to FIG. 3, the MEIS subsystem 300 includes a magnetometer 330, a system computer device 320, MEIS circuitry 330, calibration circuitry 310, a power amplifier 302, a differential amplifier 312, a feed line conductor 342, a return line conductor 344, a sense line 346, among other electronic circuitry (not shown), all of which are preferably housed in a single cabinet. Operation of the MEIS subsystem 300 is also described in further detail with respect to FIG. 6.

One illustrative MEIS subsystem which can be utilized for characterizing leakage currents on pipeline structures is described in U.S. Pat. Nos. 5,087,873 and 5,126,654 to Murphy et al, the contents of which are incorporated herein by reference in their entirety. A person of ordinary skill in the art will appreciate that any other well-known MEIS subsystem for measuring complex impedances of the pipe section and surrounding soil can be utilized.

In one embodiment, the subsystem includes a potentiostat that is preferably embodied in two add-in cards that are installed in the computer 320. The potentiostat applies a voltage between the pipe and a ground rod (ground-return electrode), and simultaneously acquires the values of on-pipe current and pipe-to-reference-electrode voltage (pipe-to-soil voltage). In this embodiment, the system potentiostat is equipped with specialized software for performing MEIS measurements.

Figure 6:
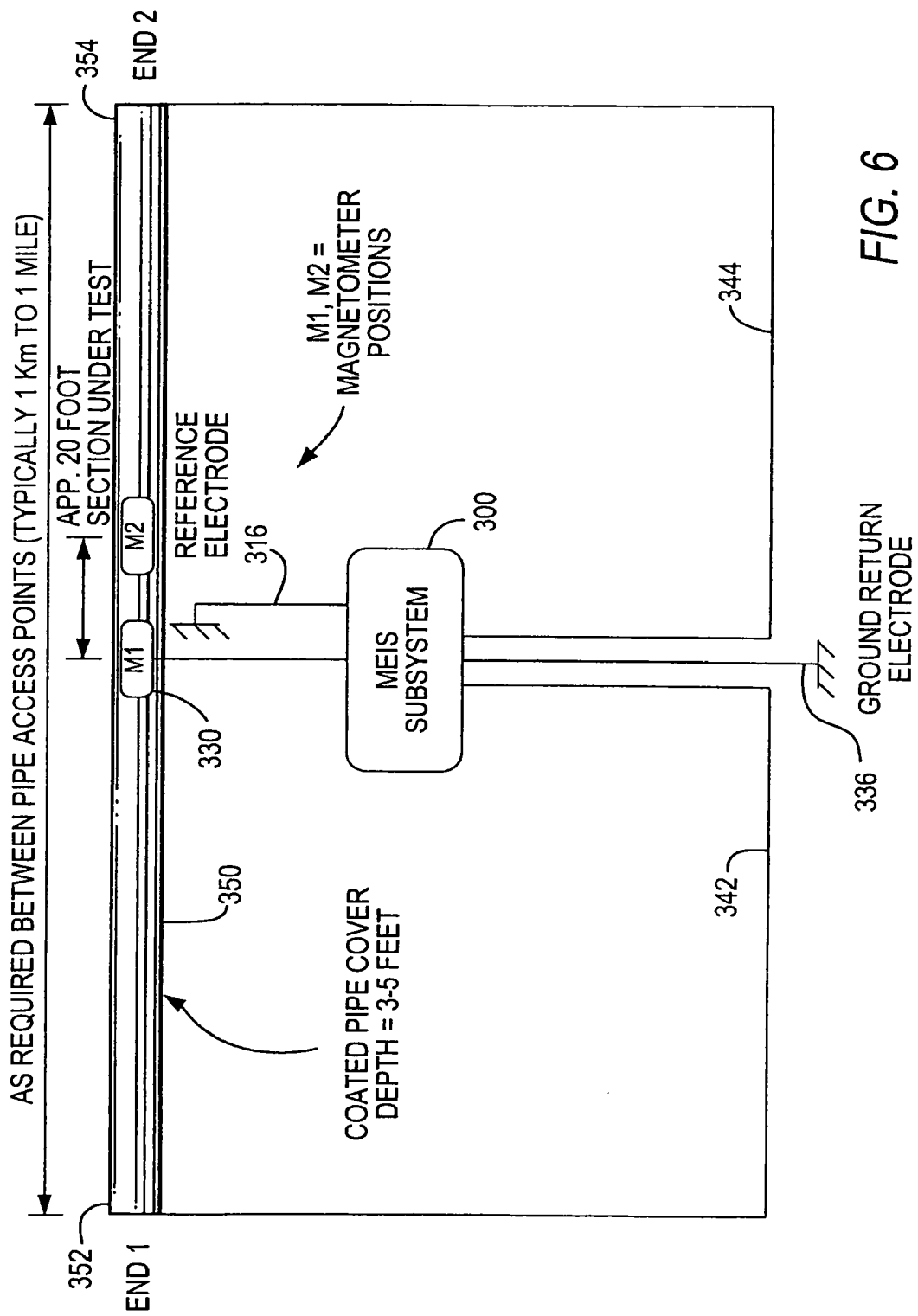
FIG. 6 is a schematic view of an illustrative layout for performing MEIS inspection of a buried pipe section under test.

In this embodiment, as indicated in FIG. 6, connections are made to the pipe at CP test points or other access points on either side to the test location. As a result, the pipe-to-soil voltage may be measured from the down-current end (End-2) at 354 while the pipe is driven from End-1 at 352 as shown in FIG. 3. The End-2 measurement is thus free of interference from the voltage drop in the line feeding End-1.

In one embodiment, the pipe-to-ground rod circuit may be driven with large signals (+/−70 volts for example) through the use of the power amplifier 302. This results in better signal-to-noise ratios due to increased on-pipe current. In contrast, the prior art MEIS techniques used low voltages directly from a potentiostat so as to avoid polarizing any corroding area. For the case of general coating defects, large voltages can be used.

The magnetometer 330 is a highly sensitive and stable electromagnetic instrument used for measuring on-pipe current. The magnetometer 330 can be a commercially available instrument suitable for measuring the strength and directional components of a magnetic field. In one embodiment, the magnetometer is a model DFM100G2, manufactured by BILLINGSLEY MAGNETICS of Brookeville, Md., USA.

The magnetometer 330 is a relative instrument that must be calibrated prior to taking actual measurements. The magnetometer 330 is electrically connected to the MEIS subsystem 300 through an interface 332. Calibration (and data acquisition) is preceded by auto-nulling the system magnetometer. This cancels out offsets from the earth's magnetic field, which could otherwise overdrive the magnetometer output. A complex calibration factor is then collected for each frequency.

As described below, it has been observed that some pipes can carry substantial amounts of power line ground-return current. In some cases, the 60 Hz signal component in the magnetometer output would overdrive the MEIS system input, or would mask the much lower level of MEIS current. Optionally, in one embodiment, an interference suppression circuit 1400, such as a Phase-Lock Loop (PLL) circuit, provides a 60 Hz sinusoidal signal to suppress or cancel out the interfering 60 Hz component of the magnetometer signal originating from power lines. Details of the PLL circuit 1400 are described below with respect to FIGS. 14 and 15.

Referring to FIG. 6 in conjunction with FIG. 3, a pipeline 350 is buried, illustratively, 3-5 feet beneath the surface of the ground, although such pipeline depths are not considered as being limiting. Testing for coating defects is conducted over sections of the pipe having test lengths of approximately twenty (20) feet, although other pipe sections lengths can be tested as well.

The magnetometer 330 is placed directly over the buried pipe 350 at a first test location (M1) between a first and second pipe ends 352 and 354 of the pipe section 350 under test. A reference electrode 316 of the MEIS subsystem 300 is inserted into the soil near the area (M1-M2) of the section of pipe 350 under test. A ground-return electrode (e.g., ground rod) 336 of the MEIS subsystem 300 is inserted into the soil from the pipeline section 350 sufficiently far from the test area (M1-M21) so as to avoid sensing any ground return current with the magnetometer. A first power (feed-line) conductor 342 is coupled from the MEIS subsystem 300 to the first end 352 of the pipe section 350. Similarly, a second power (return line) conductor 344 is coupled from the MEIS subsystem 300 to the second end 354 of the pipe section 350. This layout enables a highly versatile method for performing MEIS test measurements at any location between rectifier stations.

In one embodiment, the computer 320 includes data processing circuitry and software programs (not shown), including one or more data processing and application programs stored in memory for operating the MEIS subsystem 300 during calibration and test modes of operation. The application programs control the functions of: (a) driving the pipe with either voltage or current at pre-selected frequencies and drive levels, where in one embodiment, the pre-selected frequencies are in a range of 1 Hz to 1 KHz; (b) measuring a calibration factor for the magnetometer 330; (c) measuring the equivalent impedance (pipe-to-soil voltage/pipe current) at two locations; (d) calculating the net pipe-to-soil impedance for the pipe segment bounded by these two locations; and (e) displaying the impedance as a function of frequency in one or more graphical chart formats for data interpretation, illustratively using graphical display features of a conventional EIS program. The operation of the MEIS subsystem 300 is described below.

Pipeline Monitoring Using the MEIS Subsystem

The MEIS subsystem 300 must be calibrated prior to taking any actual field tests to compensate the magnetometer reading for cover-soil height, soil conductivity, the soil's magnetic permeability, and tilt of the magnetometer relative to the axis of the pipe 350.

The MEIS subsystem 300 includes a switching module to permit the field test operator to manually switch between the calibration and test modes of operation. During calibration, the switch S1 is manually set to calibrate mode, where data relating magnetometer output to on-pipe current is collected at each test frequency. Alternatively, during actual field testing of the pipe, the switch S1 is manually set to MEIS test mode, where a voltage is applied between the first end 352 of the pipe 350 and the ground-return electrode 336.

Testing of the pipeline using the MEIS subsystem 300 has the potential to substantially reduce the cost of pipe coating maintenance by detecting or quantifying disbanded coatings before substantial corrosion has taken place on the pipe's outer diameter. As such, the costs associated with routine replacement of pipe coating, and/or the costs of excavation to detect outside diameter (OD) corrosion can be substantially alleviated.

Referring to FIG. 3, during the test (i.e., data acquisition) mode of operation, the field test operator sets the mode switch S1 to the test mode position. A voltage is applied between the first Pipe End-1 352 and the ground-return electrode 336 using an a/c voltage signal generator (not shown) driving the power amplifier 302. The actual pipe-to-soil voltage will be less than the applied voltage due to voltage dropped in the earthing resistance of the ground-return electrode 336.

The sense line 346 provides isolation from voltage (IR) drops in the line resistance of the feed line 342. The sense line 346 allows the actual voltage at Pipe-End-1 352 to be measured directly. This is especially important for attenuative pipes, where the DPS (Down-Pipe Transmission Spectroscopy) feature is implemented. Otherwise, sensing the pipe voltage from Pipe-End-2 354 is sufficient. A switch S2 is provided for the operator to select the MEIS voltage from either Pipe-End-1 or Pipe-End-2. Live comparison of these two signals can determine if DPS is required due to down-pipe attenuation.

The differential amplifier 312 has a first input coupled to the reference electrode 316 proximate to the area (M1-M2 of FIG. 6) of the pipe being tested, and a second input coupled to the pipe 350 through switch S2. The output of the differential amplifier 312 sends a voltage signal to the computer device 320 via the MEIS circuitry 330, which is proportional to the potential difference between the selected pipe end and the reference electrode 316 to the system computer 320. The differential amplifier output represents the pipe-to-soil voltage which is used to compute the pipe-to-soil impedance, as explained in further detail below. This voltage can be collected from either end of the pipe section depending on the selection setting of switch S2. If collected from End 1 of the pipe 350, the sense line isolates this voltage from the voltage drop in the feed line resistance. The feed line input voltage (e.g., output of the power amp 302) can also be used, but this is the sum of the desired End 1 voltage and the undesired feed line voltage drop.

As mentioned previously, the function of the MEIS subsystem 300 is to estimate the condition of the pipe coating at a particular location, which can be a predetermined location based on the current leakage results previously measured by the pipe scanner subsystem 200. The condition of the pipe coating can be estimated with the MEIS subsystem 300 by measuring the net complex impedance of the pipe-to-soil junction along a segment of pipe. The impedance is measured over a range of frequencies (e.g., 1 Hz to 1 KHz), and the results can be plotted on an impedance plane presentation (Nyquist plot), as illustratively shown below with respect to FIGS. 9A-9F.

Figure 9C:
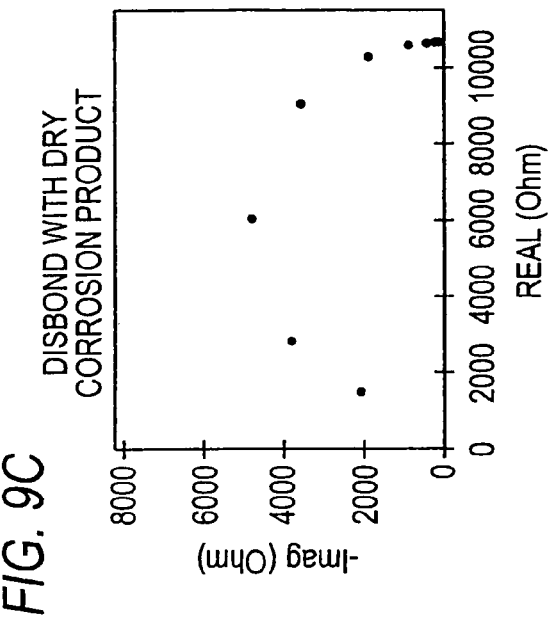
FIGS. 9A-9F are graphical representations of an impedance plots illustrating normal bonds, disbonds, micro-cracking and holidays occurring on a buried pipe section under test.
Figure 9D:
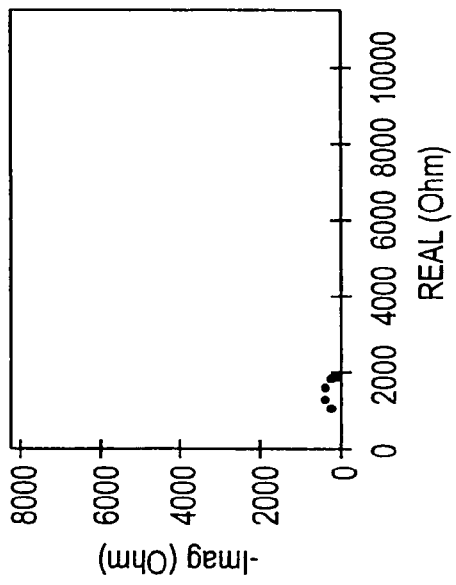
Figure 9A:
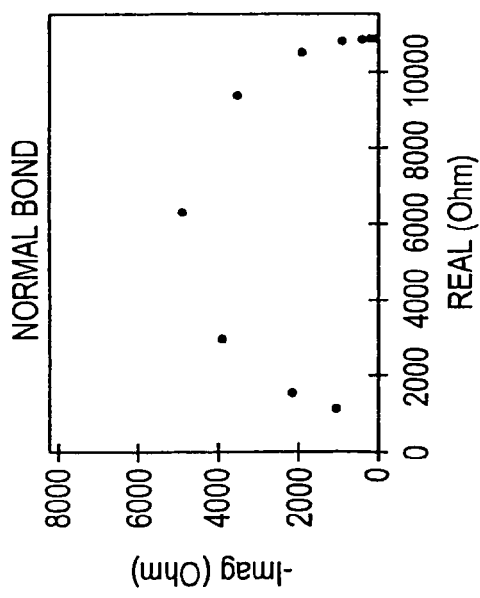
Figure 9B:
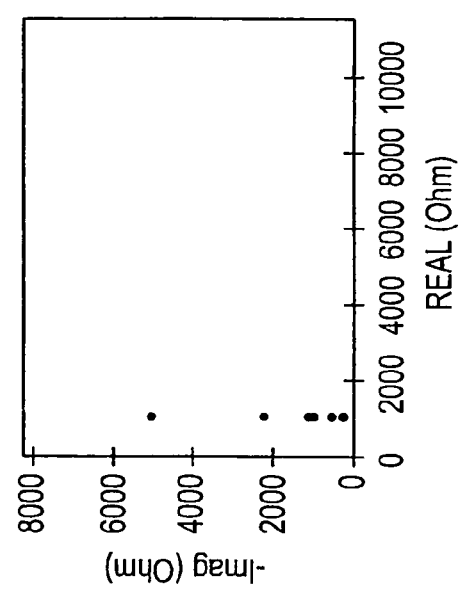
Figure 9E:
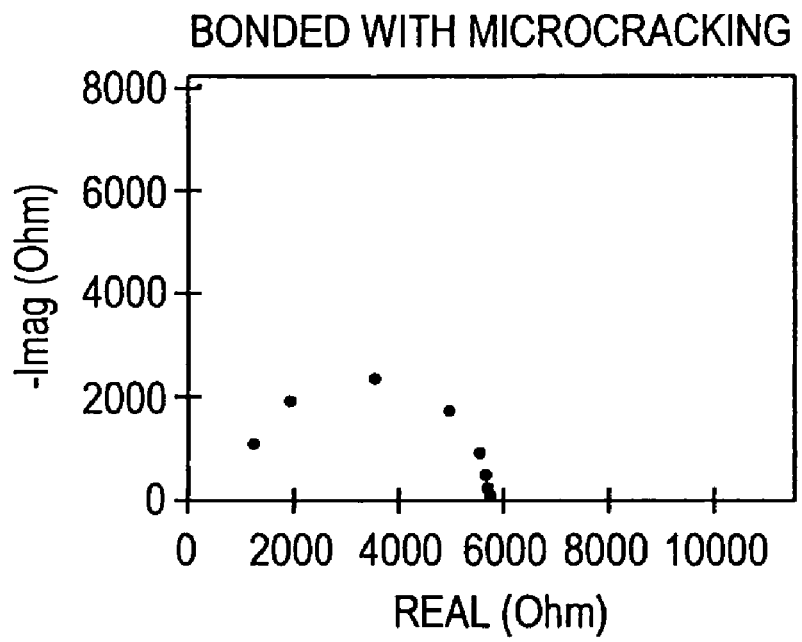
Figure 9F:
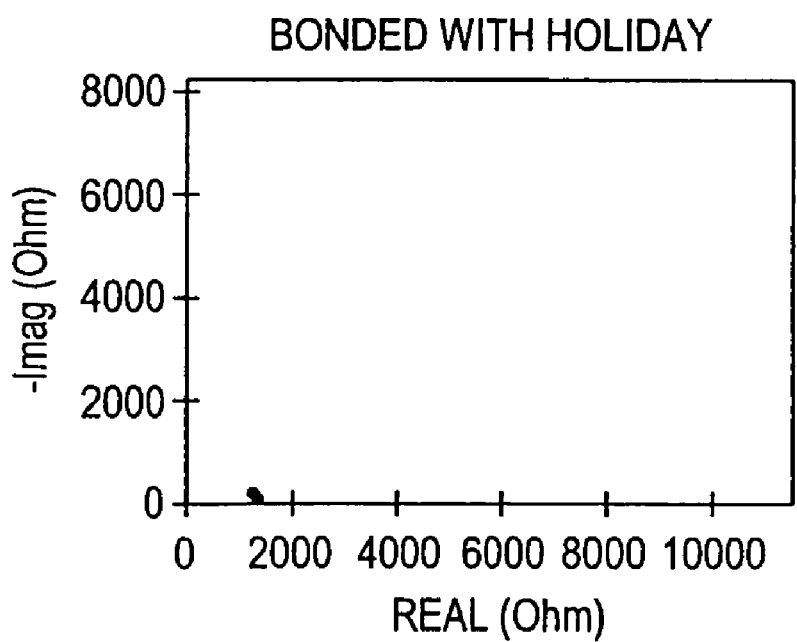

Referring to FIGS. 9A-9F, the pipe-to-soil impedance, which is measured in Ohms, is composed of a real and an imaginary part. The Nyquist plot is a chart 700 formed by plotting the real part of impedance (resistance) on the abscissa (Z axis) and the imaginary part (reactance) on the ordinate (Y axis) of a graph 700 for each frequency. FIG. 9A illustrates a possible pipe-to-soil impedance for a normally bonded coating, and FIGS. 9B-9F respectively illustrate possible pipe-to-soil impedances for an air-filled disbond, a disbond with dry corrosion product, a water-filled disbond, a bonded coating with micro-cracking, and bonded coating with a holiday.

Figure 7:
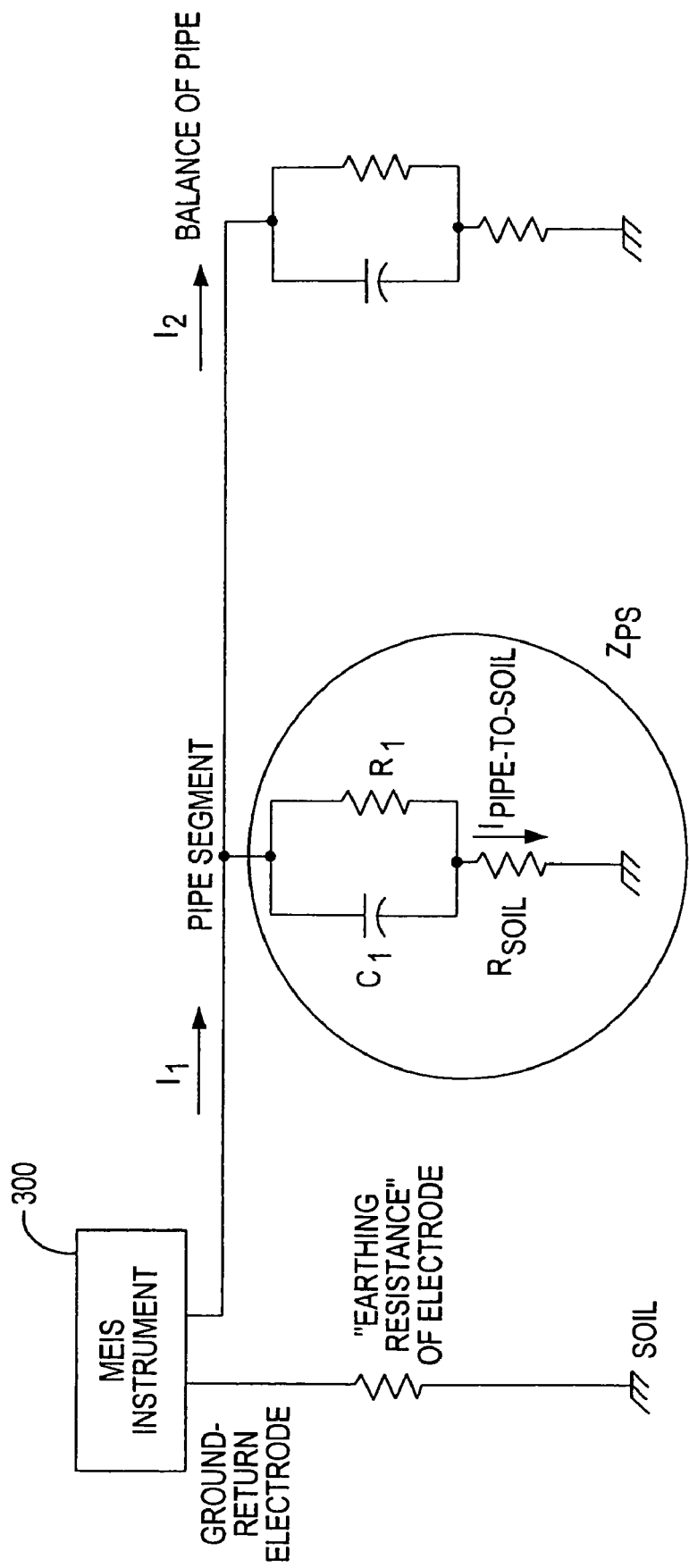
FIG. 7 illustrates a circuit model of the pipe-to-soil impedance between the buried pipe section under test and the surrounding soil.

FIG. 7 illustrates an equivalent circuit of impedance elements between the pipe and ground for a segment of pipe. This is the well-known Randles circuit, but more complex circuits may be used if necessary. The impedance at a minimum frequency (e.g., 1 Hz) is the sum of $R_1$ (pipe-to-soil resistance) and $R_{SOIL}$ (earthing resistance of the pipe segment while the impedance at the maximum frequency (e.g., 1 KHz) is approximately equal to $R_{SOIL}$. Pipe-to-soil capacitance $C_1$ equals $\frac{1}{2}\pi f R_1$, where "f" is the frequency at which the maximum imaginary impedance occurs. Alternatively, the complex admittance of the data (inverse of impedance) can be plotted to show certain features.

As described above, a two-step procedure is performed at each measurement location M1, M2. The first step is to place the magnetometer 330 over the pipe and calibrate the magnetometer 330 to read on-pipe current.

The second step is to apply a voltage to the pipe-soil junction and record the pipe-to-soil voltage (pipe-to-reference electrode voltage) $V_1$ and on-pipe current $I_1$ at each test frequency. During this step, the equivalent impedance $Z_1=V_1/I_1$, is determined at each test frequency (as described by the Murphy patents and the Murphy and Srinivasan literature set forth above). This procedure is repeated at the second measurement location M2 to produce an equivalent impedance $Z_2=V_2/I_2$ at each frequency.

The net pipe-to-soil impedance $Z_{ps}$ of the segment under test can then be calculated and analyzed as prescribed by the above-noted Murphy and Srinivasan documents. This value is available from elementary circuit analysis procedures. Specifically, $Z_{ps}$ is calculated as $V_{ps}/I_{ps}$, where $I_{ps}$ is the pipe-to-soil current exiting the pipe between the measurement locations as shown in FIG. 6. Since $V_{ps}=V_1=V_2$ (for non attenuating pipes), and due to Kirchhoffs current law $I_{ps}=(I_1-I_2)$, $Z_{ps}$ may be defined as $Z_{ps}=V_1(I_1-I_2)$.

The data processing unit (not shown) of the computer device 320 is configured for recording impedance values, and thereby records the values $Z_1$ and $Z_2$ during the measurement process. However, the above equation can be restructured by the computer 320 in terms of these impedances by substituting $V_1/Z_1$ and $V_2/Z_2$ respectively for $I_1$ and $I_2$, resulting in $Z_{ps}=Z_1 Z_2/(Z_2-Z_1)$. This latter equation is implemented on command by the system software to produce the desired data at each test frequency.

The pipe-to-soil impedance $Z_{ps}$ can be analyzed using graphical representations such as Nyquist plots that plot the results as either impedance or admittance to determine coating conditions of the measured segment, as discussed above with respect to FIGS. 9A-9F. The test operator can utilize a number of visual features of the plots along with numerical analysis of the data presented to interpret coating conditions.

Figure 8:
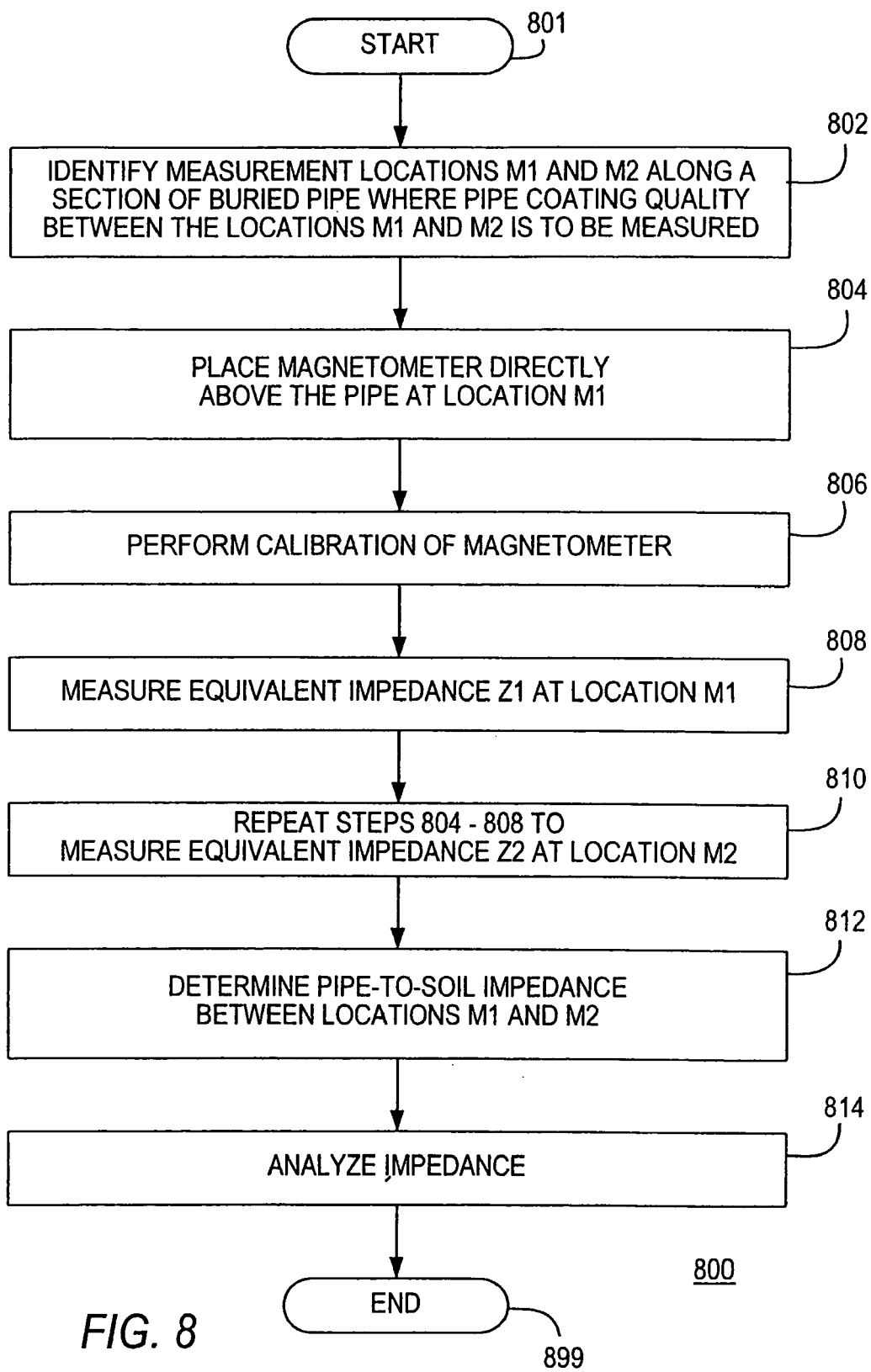
FIG. 8 is a flow diagram of a method for performing pipeline coating inspection using the MEIS subsystem in accordance with the layout of FIG. 6.

An alternative way of describing MEIS field procedure is reflected in FIG. 8. This figure is a flow diagram of the method 800 for performing pipeline coating inspection using the MEIS subsystem in accordance with the layout FIG. 6. The method 800 starts at step 801, where a section of pipe to be analyzed for coating quality is identified. At step 802, measurement locations M1 and M2 (see FIG. 6) along the pipe are determined. The measurement locations M1 and M2 identify the pipe segment over which the pipe coating quality is to be measured.

At step 804, the magnetometer 330 is placed directly above the pipe at location M1. The method then proceeds to step 806, where the magnetometer 330 is calibrated. A complex calibration factor relating magnetometer output to on-pipe current is calculated for each test frequency. At step 808, the equivalent impedance is measured at the M1 location. Preferably, the computer system 320 includes software routines capable of applying a voltage between the pipe and the ground-return electrode and acquiring the pipe to soil voltage at each of the test frequencies. The system then calculates the equivalent impedance $Z_1$ at each frequency using the acquired voltage and the on-pipe current, which is derived by multiplying the magnetometer output by its calibration factor.

At step 810, the equivalent impedance is measured at the location M2, which results in the value $Z_2$ for each frequency. The method then proceeds to step 812.

At step 812, the average pipe-to-soil impedance ($Z_{ps}$) between these locations M1 and M2 are determined for each frequency. Preferably, the computer system 320 further includes a software routine to compute the average pipe-to-soil impedance, where $Z_{ps}=Z_1 Z_2/(Z_2-Z_1)$.

At step 814, the measured and computed results (data) are analyzed to determine the quality of the pipe coating. Preferably, a graphical representation is generated by plotting $Z_{ps}$ on a complex impedance plane (a Nyquist plot) or an admittance plane. Thereafter, visual and/or numerical analysis of the data is conducted in a conventional manner to determine coating properties.

The system 300 includes programs that include provisions for analyzing $Z_{ps}$ data in several ways. Preferably, the procedure utilizes Nyquist plots within 1:1 ratios, although other ratios can be utilized.

The analysis of these plots is conducted from both a visual pattern recognition approach, and from review of the numerical data on the chart. Examples of possible Nyquist plots for pipe coating are provided in FIGS. 9A-9F.

Referring now to the Nyquist plots of FIGS. 9A-9F, initial decisions on coating quality and locations for subsequent MEIS testing can be made using the system software which has provisions for analyzing $Z_{ps}$ data in several ways. A Nyquist plot contains real impedance on the horizontal axis and imaginary impedance on the vertical axis.

The analysis of these plots is conducted from both a visual pattern recognition approach, and from review of the numerical data on the chart. Parameters of significance for Nyquist plot analysis include: (i) real impedance at the minimum test frequency. It is noted that for the standard circular response shown, this value will be the sum of pipe-to-soil resistance and the soil resistance, or $R_1+R_{SOIL}$; and (ii) real impedance at the maximum test frequency. For the standard circular response shown, this value will be the soil resistance, or $R_{SOIL}$; and maximum imaginary impedance at the top of the circular trace. This value will be half of the impedance of the pipe-to-soil capacitance. The capacitance ($C_1$) can be computed knowing the frequency at which the maximum impedance is generated. The above relationships between the Nyquist plot and circuit parameters of a Randles circuit are well known to those of ordinary skill in the art.

Alternatively, the capacitive and resistive circuit elements of $Z_{PS}$ can be calculated from impedance fitting software normally employed for EIS work. Examples include ECHEM ANALYSIS software available from GAMRY Instruments of Warminster, Pa., USA and ZSIMPWIN software, available from Princeton Applied Research of Oak Ridge, Tenn., USA.

Possible Nyquist plots for various coating conditions are shown in FIGS. 9A-F. These are based on assumptions regarding the impact of anomalies on the impedance, and were generated using laboratory Randles circuits to simulate short sections of pipe. It is noted that some field results may vary from these assumptions.

Pipeline Coating Field-Test Simulator

The present invention includes providing one or more field test simulators in the form of sections of pipe simulating normal and defective pipe coatings, which can be used to monitor how the MEIS system will respond to pipe coating anomalies and holidays in different types of soil environments. The pipe samples of the present invention are buried in various soil environments at predetermined depths. The field test simulators (pipe samples) provide a baseline from the known pipe samples to ensure the MEIS subsystem 300 is properly identifying any coating anomalies in the actual pipe sections being tested. The baseline information can vary for different sized pipe samples, different sizes of simulated disbonds, and soil environments. The impedance for the pipe samples is measured over a range of frequencies (1 Hz to 1 KHz for example), and the results can be plotted on an impedance plane presentation (Nyquist plot), as illustratively shown below in FIGS. 9A-9F.

Each pipe sample with a simulated disbond includes a material having a low dielectric coefficient wrapped on a section of the pipe prior to wrapping the pipe with tape. The low dielectric coefficient material simulates an air-filled disbond. A preferable material for this application is closed-cell sponge rubber sheeting, such as DURAFOAM™, which can be supplied in sheets of specified thickness and has a dielectric coefficient approximating that of air. A person of ordinary skill in the art will appreciate that other materials having dielectric coefficients close to that of air can also be utilized. Further, other materials having dielectric coefficients approximating a disbond with moisture or a holiday can also be used in fabricating the pipe samples. The material is wrapped around the pipe sample prior to standard tape wrapping of the pipe. As a result, there is a volume under the tape whose contribution to pipe-to-soil capacitance is substantially equal to that of an air gap of the same dimension. The resistance of this interface is not addressed with the low dielectric coefficient material.

The method for fabricating the pipe simulation sample advantageously includes contemporaneous use of the above-described tape wrapping deployed in the intermediate section of the pipe extending between opposing end caps to create synthetic disbonds and a multi-component epoxy coating on the end sections of the pipe. The latter provides both superior sealing of electrical connections and a non-deformable surface for gripping and supporting the pipe sample.

Figure 10:
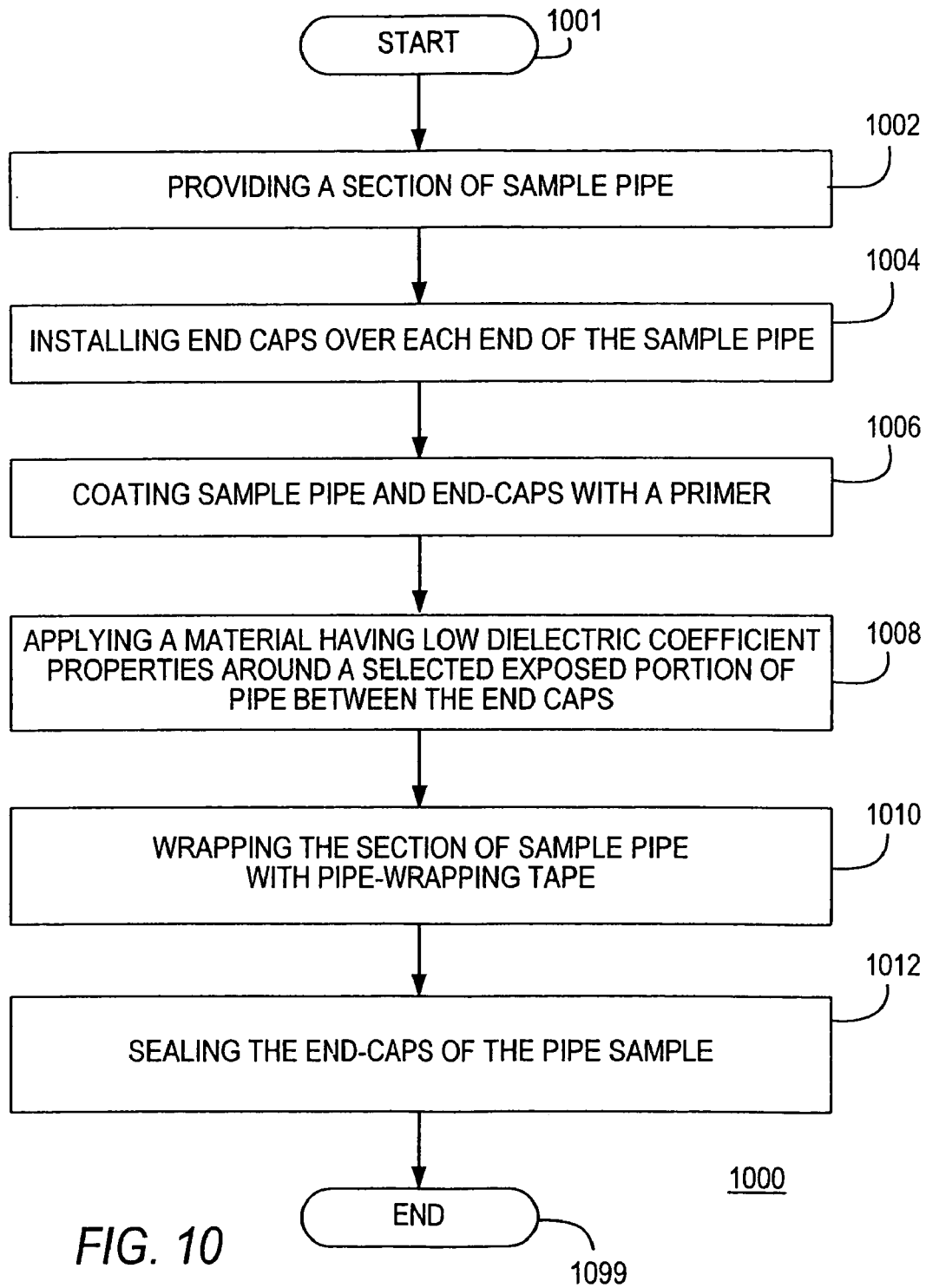
FIG. 10 is a flowchart of a method for fabricating a calibration sample for calibrating the MEIS subsystem.

A flowchart of a method 1000 for producing a simulated pipe sample is illustrated in FIG. 10. The method 1000 begins at step 1001, and proceeds to step 1002 where an elongated pipe segment having a predetermined length and diameter is obtained for use as a pipe sample. The pipe segment can have a length in the range of 10 to 30 feet and a diameter of 9 to 36 inches, although such dimensions are not considered limiting. The metal composition of the elongated pipe sample is preferably the same or similar to the pipe section or structure being tested in the field. However, the pipe sample does not have to match the actual pipe section being tested. Rather, the pipe sample need only be fabricated from a conductive material, such as a steel alloy.

At step 1004, end caps are placed over each end of the pipe sample. Preferably, the end caps are welded to the pipe ends and an electrical conductor extends outward from each cap. At step 1006, any exposed metal of the pipe sample, including the opposing end caps, are coated with a primer.

At step 1008, a section of a material having a low dielectric coefficient is placed around the intermediate area of the pipe sample between the end caps to simulate air-filled disbonds of various sizes. At step 1010, the entire pipe sample with the simulated disbond is wrapped in pipe-wrapping tape (e.g., 1 or 2 layers of pipe wrapping tape). At step 1012, the end-caps of the pipe sample are sealed to prevent moisture ingress. In particular, the opposing end-caps are sealed by pipe wrapping tape and silicon. At step 1099, the method 1000 ends.

Figure 11:
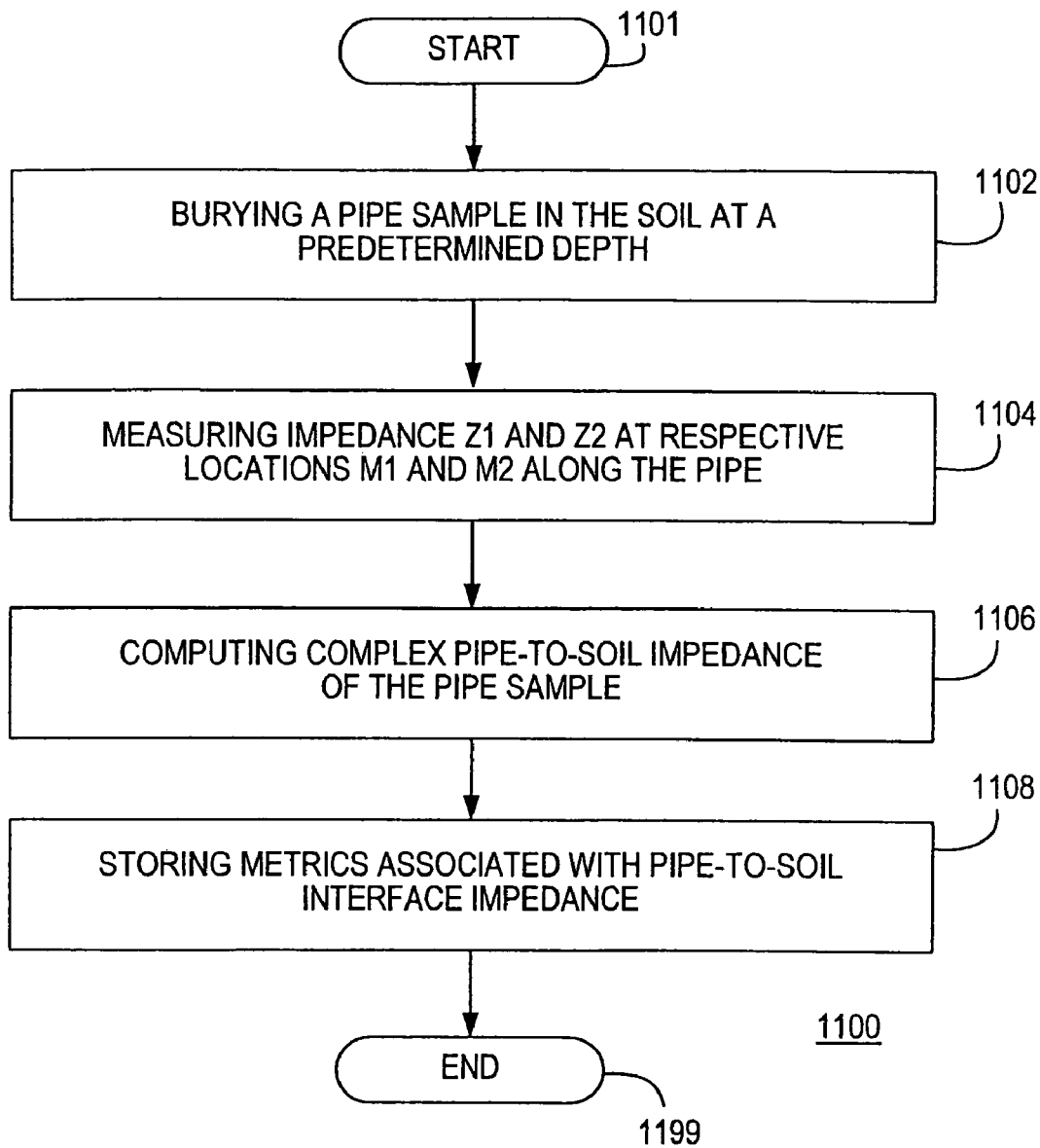
FIG. 11 is a flowchart of a method for using the calibration sample fabricated by the method of FIG. 10 for calibrating the MEIS subsystem.

FIG. 11 is a flowchart of a method 1100 for simulating field conditions of a pipe buried in various soil environments using a pipe sample fabricated by the method 1000 of FIG. 10. The pipe samples can be used for determining the MEIS response in the particular soil environment in which they are buried, or can be used for determining the system response to various sizes of simulated disbonds, holidays, micro-cracking or other pipeline coating defects. Accordingly, the calibration provides a baseline on a known pipe sample to ensure the MEIS system is properly identifying any disbonds, holidays or micro-cracks in the actual pipe sections being tested.

The method 1100 begins at step 1101, where one or more pipe samples are fabricated in accordance with the procedure 1000 of FIG. 10. It is noted that one or more pipe samples can include a reference sample not having any simulated disbonds. At step 1102, a pipe sample is buried in the soil at a predetermined depth. A trench having a length greater than the pipe sample is preferably used so that the wires feeding opposing Ends 1 and 2 of the pipe can be laid in the trench extensions. The M1 and M2 locations for the system magnetometer can then be selected beyond the pipe ends if necessary. In this case, the on-pipe current upstream and downstream from the simulated disbond can also be sensed over the feed wires, as well as over the pipe.

At step 1104, the magnetometer 330 is placed over the pipe sample at locations M1 and M2, respectively, and calibration and impedance measurements of Z1 and Z2 respectively are performed at each location. At step 1106, the MEIS subsystem 300 computes the average complex impedance of the pipe segment, as described above.

At step 1108, the metrics associated with the pipe-to-soil interface impedance is stored, for example, in the computer device 320 for future reference. More specifically, the test data can be used to predict or estimate $Z_{PS}$ behavior for coating disbonds in operational pipelines buried in the same soil type. At step 1199, method 1100 ends.

Advantageously, the pipe samples can vary in length and diameter, and the thickness of the low dielectric coefficient material can also be varied to emulate different degrees of a disbond. Further, the different sized/material thickness pipe samples can be buried in different types of soils, such that method 1000 can be performed for each different pipe sample to generate a database of simulated disbonds. The results can be subsequently used to identify disbonds occurring on the actual pipe buried in the field.

Pipeline Coating and Cover Soil Bench-Test Simulator

Figure 12:
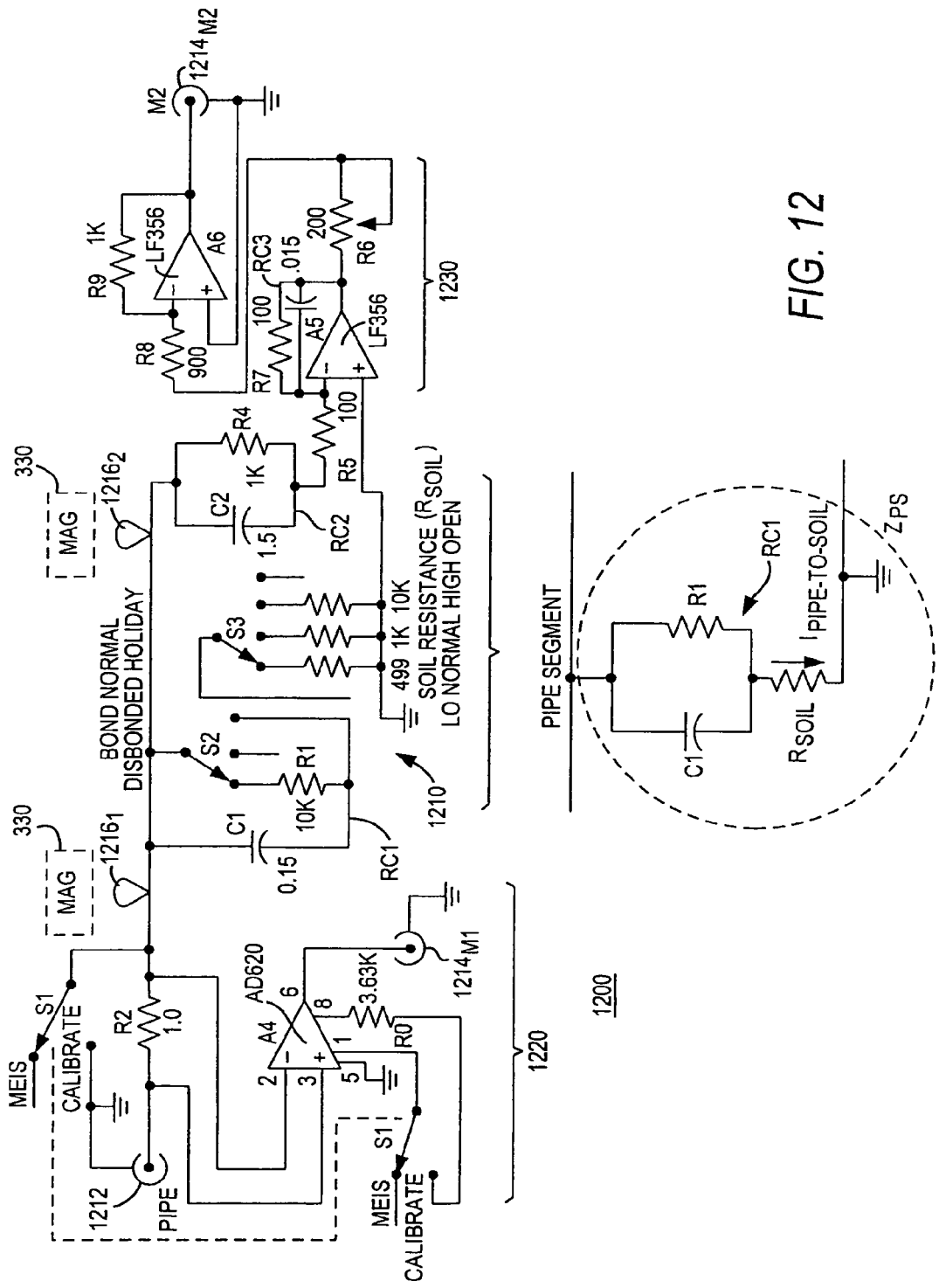
FIG. 12 is a schematic diagram of a pipe coating simulator of the present invention for simulating electrical pipe-to-soil impedance of a coated pipe segment.

In another embodiment of the invention, a pipe-coating simulator is provided for testing and calibrating the MEIS subsystem 300, for example, in a laboratory or bench environment, as opposed to operation in the field. An illustrative schematic diagram of a pipeline coating simulator 1200 which simulates the electrical pipe-to-soil impedance of a coated pipe segment is shown in FIG. 12. Additionally, an illustrative schematic diagram of a cover-soil simulator 1300 which simulates the electromagnetic effects of the cover soil on the electromagnetic field of the pipe current is shown in FIG. 13. In one embodiment, the circuitry of the pipeline coating (i.e., pipe-to-soil) simulator 1200 and cover soil simulator 1300 are housed in a common cabinet. Alternatively, the circuitry of the pipe-to-soil simulator and cover soil simulator can be housed independently.

The circuitry of FIG. 12 simulates pipe current flow under three coating conditions that including normal, disbond and holiday coating conditions with several levels of simulated soil resistance. The main input (i.e., current injection point) simulates an electrical connection to a pipe, while the M1 and M2 outputs simulate the signals expected from magnetometers located at the first and second locations along the pipe section under investigation. M1 simulates the magnetometer that is up-current from the segment under measurement. It represents $I_1$, which is the sum of the pipe-to-soil currents flowing from the voltage injection point (PIPE) in (i) the segment under test and (ii) the balance of the pipe located down-current from the injection point (PIPE in drawing). M2 represents only $I_2$, which is the current flowing in the balance of the pipe. The difference of M1 and M2 represents the complex current flowing from the pipe to soil in the test area. That is, the desired current $I_{ps}$ is the vector difference of $I_1$ and $I_2$. Dividing the input voltage by this current yields the simulated pipe-to-soil impedance $Z_{ps}$. The pipe simulator can be used to calibrate the MEIS subsystem 300, and more specifically, the potentiostat of the MEIS subsystem 300.

Referring to FIG. 12, the pipeline coating simulator 1200 simulates measured on-pipe current under various conditions of pipe-to-soil impedance and provides simulated magnetometer test points M1 and M2 representing the two measurement locations as described with respect to FIG. 6. Accordingly, the simulator 1200 can be used to simulate a pipe segment with various coating conditions and soil conditions. In one embodiment, the magnetometer 330 is decoupled from the MEIS subsystem 300 and conductors 332 of the MEIS subsystem 300 are electrically coupled to either test point $1214_{M1}$ or $1214_{M2}$ through an adapter. Alternatively, the simulator 1200 can be used with a magnetometer 330 by placing the magnetometer within sensing range of a current-loop wire 1216.

For example, the current-loop wire $1216_1$ enables the magnetometer 330 to sense the current at the injection point 1212, while the current-loop wire $1216_2$ enables the magnetometer 330 to sense the current down-pipe at M2, which represents the difference between the injected current and the simulated leakage currents through the pipe coating and soil circuitry 1210. The pipeline coating simulator 1200 can be used to conduct bench testing of the MEIS subsystem 300 in either calibration or test modes of operation.

A current source or voltage source is provided at the insertion point 1212, illustratively labeled "PIPE" in FIG. 12. The leakage current though the pipe coating is simulated by the RC circuitry RC1 controlled by switch S2, while the soil environment is simulated by soil resistances $R_{SOIL}$ controlled by switch S3 of circuitry 1210. The pipeline coating simulator 1200 has two magnetometer location test points, M1 and M2, which simulate the locations M1 and M2 where the magnetometer is positioned along a pipe segment under test in the field, as illustrated in FIG. 6.

Referring to FIG. 6 along with FIG. 12, the M1 test point $1214_{M1}$ represents the injection current $I_1$, which is the input current to the pipe segment, while M2 test point $1214_{M2}$ represents the down-pipe current $I_2$, which is the current leaving the segment into the balance of the pipe. Like MEIS testing in the field, the desired pipe-to-soil current needed for further calculations, $I_{PS}$, is equal to the vector quantity $I_1$ minus $I_2$. The pipe-to-soil current $I_{PS}$ is simulated by the circuitry 1210 of the simulator 1200.

Referring again to FIG. 12, the circuits 1220 and 1220 comprise current-to-voltage converters which simulate the M1 and M2 magnetometer outputs. These simulated M1 and M2 outputs are respectively shown as $1214_{M1}$ and $1214_{M2}$.

The circuit 1220 comprises an instrumentation amplifier A4 (e.g., an AD620) which senses the input current as a function of the voltage drop across the 1 ohm sensing resistor R2. The A4 amplifier generates an output at $1214_{M1}$, which is one volt per amp (i.e., 1 mho in transconductance units) in the MEIS mode of operation. Higher transconductance can be obtained if needed during the CALIBRATE mode by switching in a gain resistor $R_g$ as shown. Higher gains might be needed to match any voltage gain employed by the pipe driver output of the MEIS system.

The pipe-to-soil leakage current is simulated via circuitry 1210, which includes the user selectable RC circuit RC1 and selectable resistive elements $R_{SOIL}$. A schematic representation of the pipe-to-soil current flowing from the pipe segment to ground is also shown in FIG. 12, where the capacitor C1 is coupled in parallel with resistor R1 to form RC circuit RC1, which is in serially coupled to the selectable resistor $R_{SOIL}$ to ground. This is the standard Randles interface circuit.

The type of pipe coating bond is simulated by selecting the resistor value R1 via switch S2. Resistor R1 can be a resistor having a value of, for example, 10K ohms, an open circuit and a short circuit which emulate a normal bond, a disbond, and a holiday type pipe condition, respectively. Alternatively, a first potentiometer can be used in place of the resistive, open and shorted elements.

The RC circuit RC1 is serially coupled to ground via a resistive element $R_{SOIL}$ by switch S3 to emulate the various soil environments by providing a plurality of resistive elements, which signify various soil conditions. For example, switch S3 can be a 4-way switch that can be set to one of three resisters having values representing low, medium, and high soil resistive conditions. In one embodiment, a low resistor value is provided by a resistor having a resistance in a range of 1 to 499 ohms, the medium resistor value is provided by a resistor having a resistance in a range of 500 to 10K ohms, and the high resistor value is provided by a resistor having a resistance greater than 10K ohms to 1M ohms. A fourth switch setting of S3 can be an open circuit representing very high soil resistance condition. Alternatively, a second potentiometer can be used in place of the plurality of resistive elements. It is noted that switch S3 can be set in the open position to allow testing of the M2 output against the M1 output in MEIS mode to verify proper operation of the two current-to-voltage circuits. The outputs should be exactly equal in this case, since they are sensing the same current.

Accordingly, the leakage current $I_{PIPE-TO-SOIL}$ ($I_{PS}$) from a pipe segment is simulated by circuit portion 1210, which enables an operator to set the desired pipe coating and soil conditions, as required. The down-pipe current ($I_2$) is the difference from the injected current ($I_1$) at the injection point 1212 and the leakage current ($I_{PS}$). The down-pipe current ($I_2$) is monitored at test point $1214_{M2}$, which simulates the second magnetometer location as shown in FIG. 6.

The circuit portion 1230 is a current-to-voltage converter which generates the simulated M2 magnetometer output $1214_{M2}$. The simulated down-pipe current $I_2$ is developed through the simulated balance-of-pipe impedance consisting of C2, R4 and R5. These impedance values are selected to be much less than those circuit portions 1210 (i.e., C1, R1 and $R_{SOIL}$), so as to represent a longer section of pipe. The current $I_2$ flows from the "PIPE" 1212 through the simulated balance-of-pipe circuit to a virtual ground represented by the inverting input of Op Amp A5. The circuitry associated with Op Amps A5 and A6 convert this current to a voltage with a transconductance of 1 mho (1 volt per amp) at output $1214_{M2}$. Capacitor C3 provides phase equalization (e.g., approximately 0.57 degrees at 1 KHz) so that M1 and M2 outputs are phase matched.

Figure 13A:
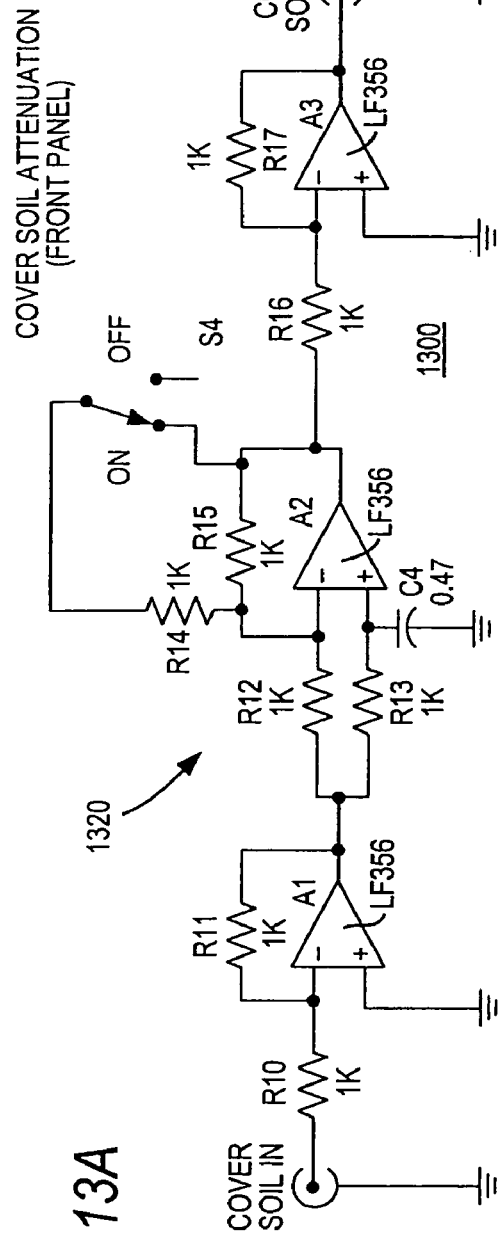
FIGS. 13A and 13B are a schematic and functional block diagrams, respectively, of a cover soil simulator of the present invention illustrating a bi-modal phase-shift bridge circuit for simulating electromagnetic effects of the cover soil on the electromagnetic field of the pipe current.

Referring to FIG. 13A, a cover soil simulator 1300 is illustratively shown. The simulator 1300 simulates the effect of cover soil conductivity and magnetic permeability. The cover soil simulator 1300 adds phase lag and attenuation to the "Cover Soil In" signal that may be encountered by the electromagnetic field of the pipe when it loops to the magnetometer through conductive or magnetic soil.

Referring to FIG. 13A, the circuitry simulates the effect of conductive or magnetic cover soil on the electromagnetic field emanating from the on-pipe current. In one case (attenuation=OFF) the signal is fed through a constant-amplitude phase shift bridge. In the other case (attenuation=ON) the signal is attenuated as well as phase shifted, simulating eddy current losses in the soil.

Figure 13B:
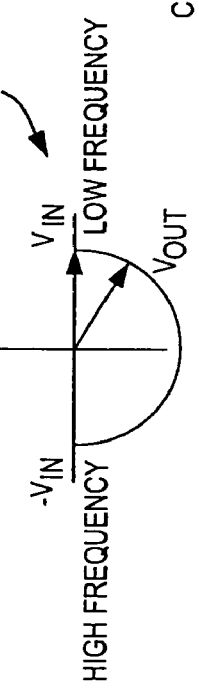
Figure 13B:
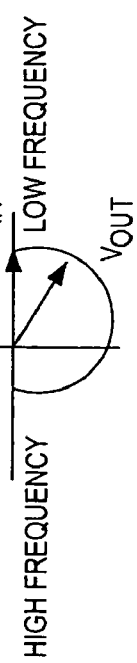

The simulator 1300 includes circuit 1320 for providing attenuation and phase shift with increasing test frequency. FIG. 13B is a functional block diagram of the bi-modal phase shift bridge of FIG. 13A located between the simulated cover soil input and output to provide such attenuation and phase shift with increasing test frequency.

Referring to FIG. 13A, the cover soil attenuation circuit 1300 illustratively includes three amplifiers (e.g., Operational Amplifiers) A1, A2 and A3 serially coupled between a cover soil input port and a cover soil output port to provide a constant-amplitude phase-shift bridge. The constant-amplitude phase-shift bridge 1320 provides phase lag, while frequency roll-off attenuation can be switched in or out.

In particular, a first Op Amp A1 serves as an inverting unity gain buffer for driving the next stage. This next stage comprised of Op Amp A2 and associated circuitry forms the well-known constant-amplitude phase shift circuit with a provision for switching in a frequency-dependent amplitude roll-off. However, with switch S4 set to OFF, Op Amp A2 functions as a differential amplifier having a DC voltage gain of +2 through the non-inverting input, and a gain of −1 through the inverting input. When both inputs are fed from the same AC signal, the output will behave as indicated by $V_{out}$ in the phasor diagram 1340. $V_{out}$ will maintain a fixed magnitude with a negligible phase shift at low frequencies. However, at a frequency of 300 Hz, its phase will lag $V_{in}$ by approximately 90°. The phase lag will continue to increase with frequency and the locus of the $V_{out}$ phasor is the circle shown in the phasor diagram of FIG. 13B.

This same phase relationship will exist between the Cover Soil In and Cover Soil Out connections, since there are two inverting unity gain buffers in the path, namely the circuits of Op amps A1 and A3. In an alternative embodiment, these inverting buffers could be dispensed with, but this would require replacing R13 with a very large inductor and C4 with a resistor in order to attain increasing lag with frequency.

When switch S4 is set to "ON", the output is no longer constant with frequency, but will roll off as indicated in phasor diagram 1341. This simulates eddy current losses in conductive soils.

Phase-Lock Loop Technology for Stray Current Suppression

As noted above with respect to FIG. 3, it has been observed that some pipes can carry substantial amounts of power line ground-return current. In some cases, the 60 Hz signal component in the magnetometer output could overdrive the MEIS system input, or mask the much lower level of MEIS current.

One solution includes stop-band filtering at 60 Hz. However, this technique is not highly practical for MEIS because the filter will interfere with other MEIS test frequencies in proximity to 60 Hz. Another solution is digital signal processing such as FFT, after which the offending signal components can be deleted. However, this requires an input dynamic range large enough to acquire the 60 Hz interfering signal, while still having adequate resolution for the small MEIS signal, which is not always practical with the potentiostat circuitry used for the MEIS subsystem 300.

Figure 14:
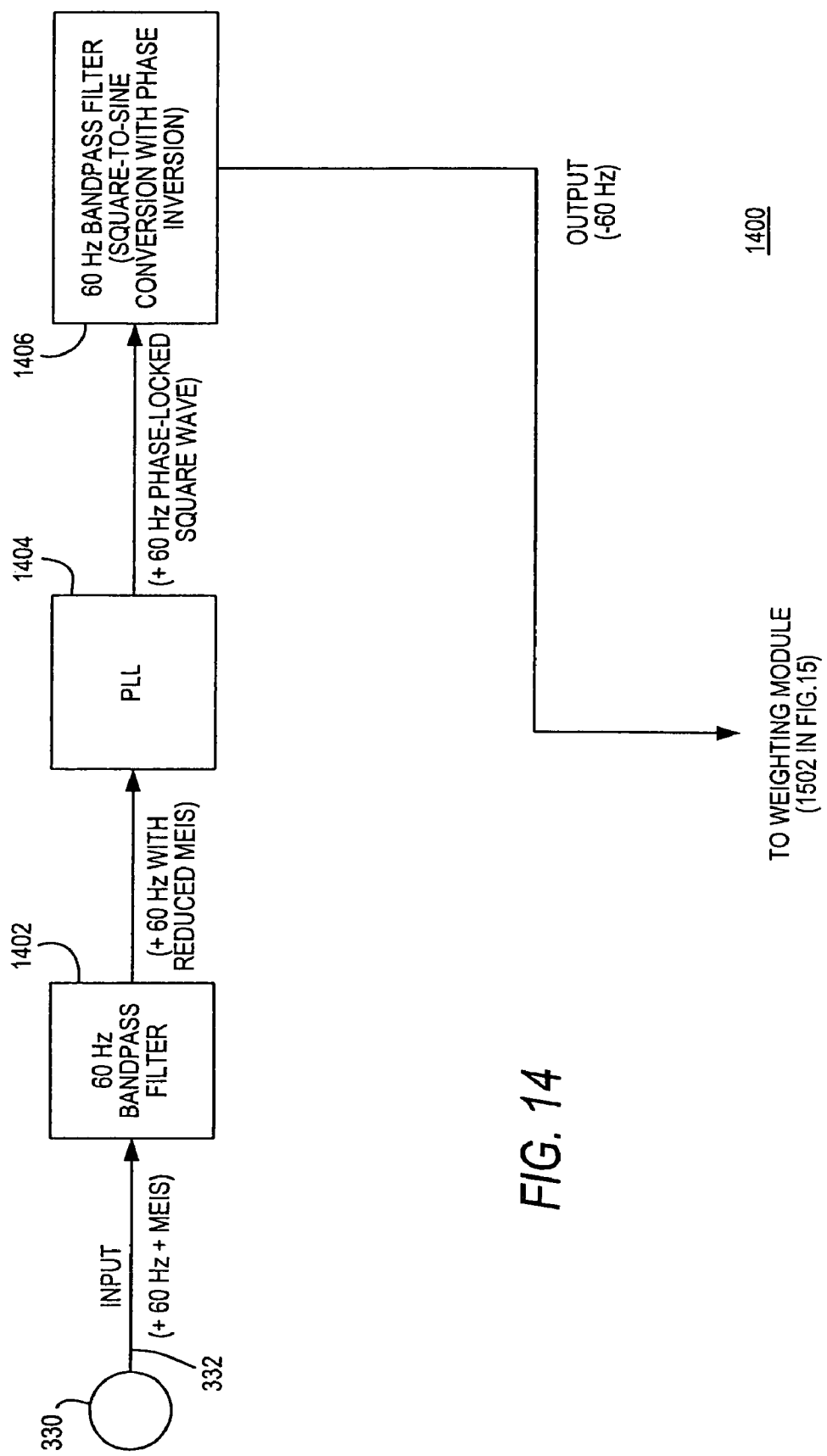
FIG. 14 is a flow diagram of a phase-lock loop (PLL) configuration for generating a phase-locked 60 Hz signal free of MEIS signals.
Figure 15:
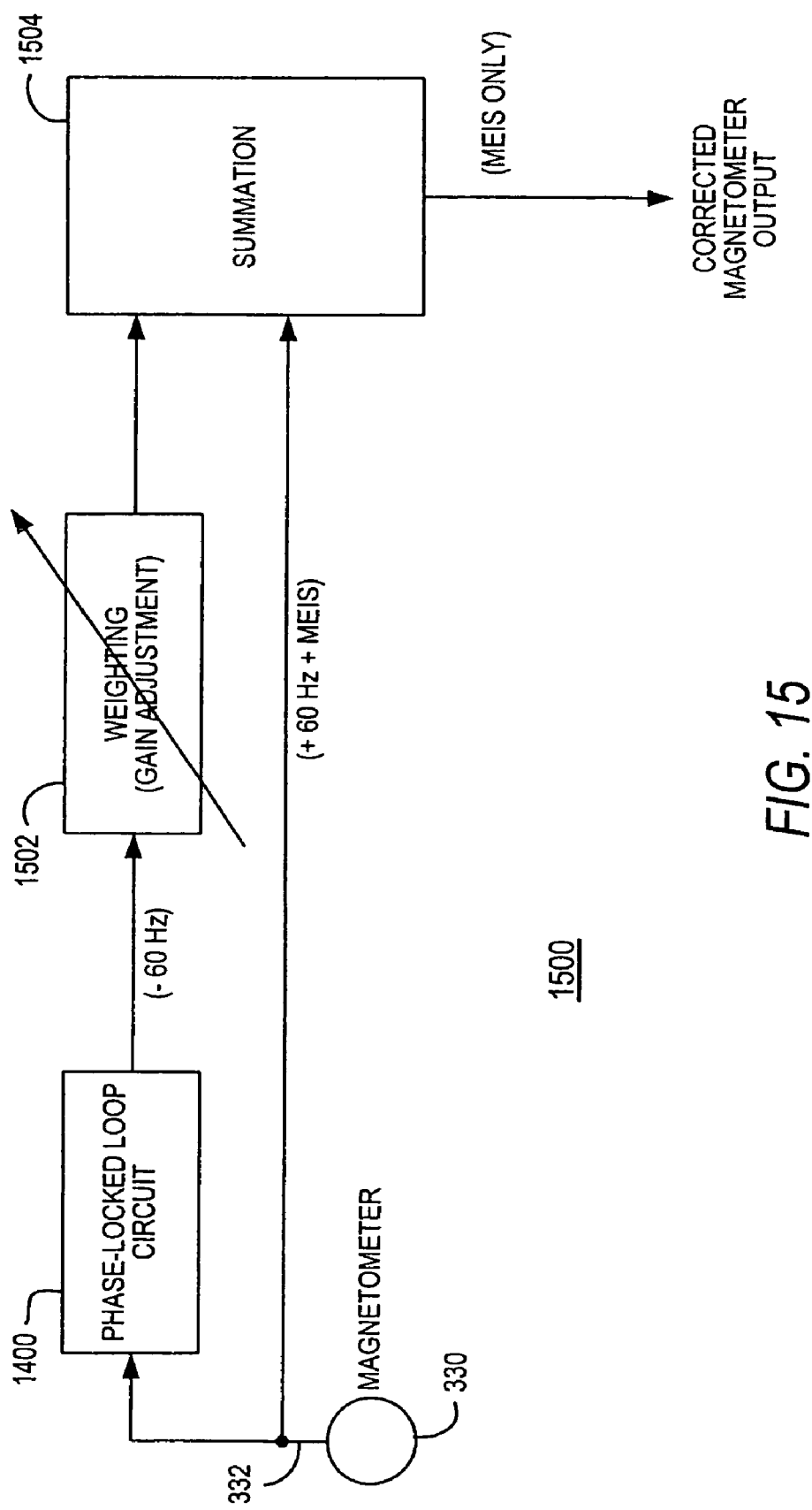
FIG. 15 is a flow diagram of a system for PLL suppression of 60 Hz interference in magnetometer signals.

Referring to FIGS. 14 and 15, an interference suppression circuits 1400/1500 (FIG. 3) can be utilized to suppress the unwanted signal to overcome the disadvantages of the 60 Hz power line signals. In one embodiment, the interference suppression circuit 1400 includes a phase-locked loop (PLL) circuit 1404 which is configured to lock on to any 60 Hz component found in the incoming MEIS signal. A band-pass filter circuit 1406 can then be used to generate a pure sinusoidal signal for cancelling the interfering signal.

Referring to FIG. 14, the interference suppression circuit 1400 includes a 60 Hz band pass filter 1402 that is provided between the input signal from the magnetometer 330 and the PLL circuit 1404. The output of the 60 Hz BP filter includes the 60 Hz signal and a reduced MEIS signal, which are fed to the PLL 1404. The output from the PLL 1404 is a +60 Hz phase-locked square wave, which is then filtered with a second band-pass filter 1406 to render it a pure sinusoid. The converted sinusoidal signal is inverted by 180 degrees (i.e., −60 Hz output signal).

Although the interfering signal is described as a 60 Hz signal, a person skilled in the art will appreciate that the present invention can be readily configured to suppress or cancel the effects of interfering current signals occurring at other frequencies. In particular, the interference suppression circuitry 1400 can include a PLL 1404 that generates a phased-locked output signal at a predetermined frequency or a predominant frequency that can be used to cancel or suppress the undesirable interference resulting from any stray current in the pipe or structure under measurement.

Referring to FIG. 15 the PLL circuit 1400 is shown incorporated into the complete interference suppression circuit, where the suppression circuitry 1500 provides 60 Hz suppression by weighing (e.g., scaling and/or phase shifting) 1502 the resulting sinusoid signal from the PPL circuit 1400, and vectorally summing 1504 the weighted output signal with the magnetometer signal (+60 Hz signal and the MEIS signal) to cancel or reduce the unwanted 60 Hz component.

Accordingly, the undesirable 60 Hz signal component from the magnetometer 330 is removed or reduced to prevent overdrive of the MEIS system input or masking the much lower level of MEIS on-pipe current. The corrected output signal (pipeline leakage current) from the magnetometer 330 is sent to the computer device 320 for further processing, as shown in FIG. 3.

Dual Magnetometer Interference Suppression

Figure 16:
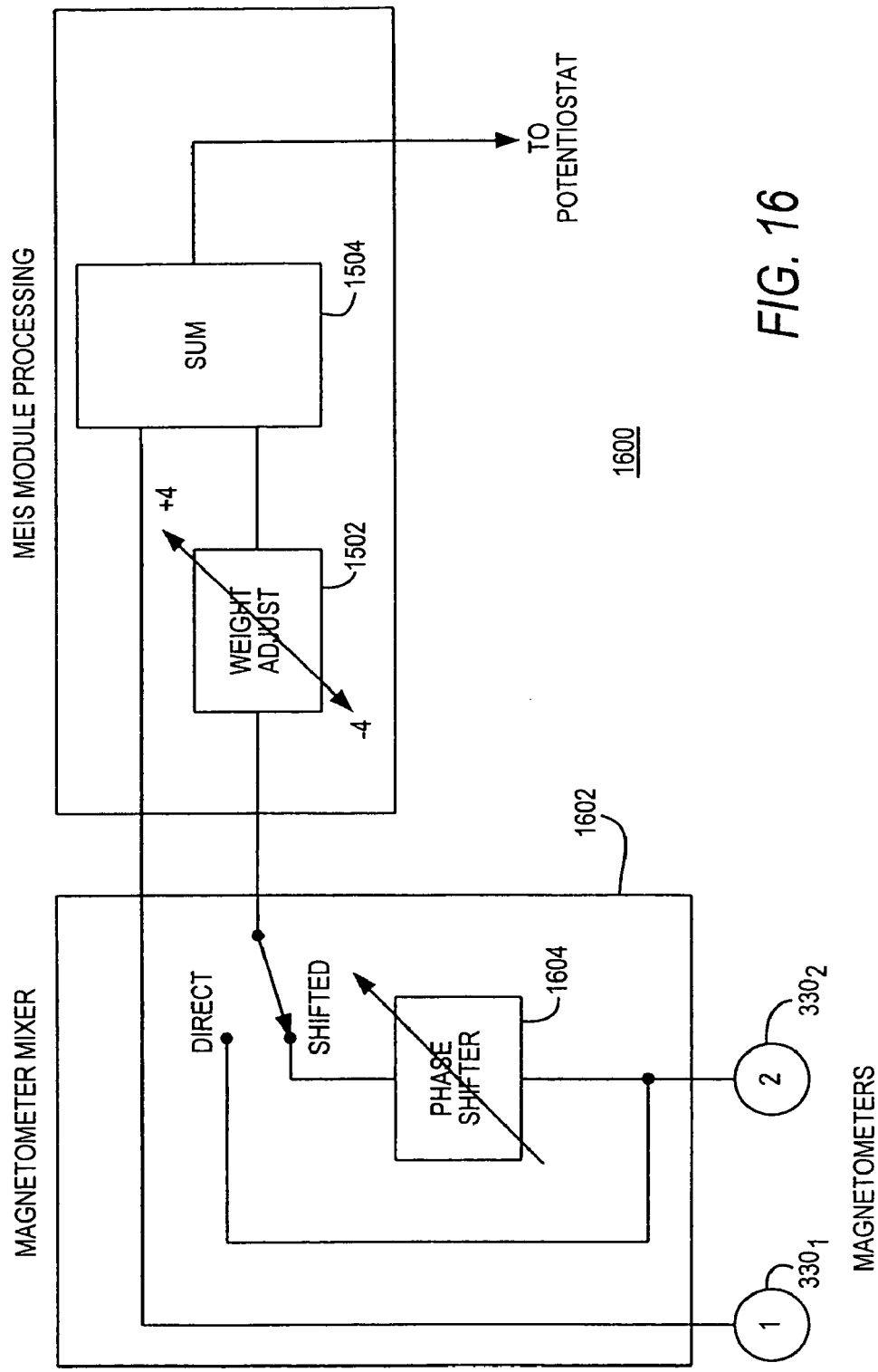
FIG. 16 is a flow diagram of a system for suppressing unwanted signals in the magnetometer output using a second 60 Hz signal from another pipe in the vicinity.

Referring to FIG. 16, an alternative interference suppression system 1600 is shown. Suppression of unwanted power line signals at the magnetometer output can also be accomplished by using a similar interference signal from another pipe in the vicinity. A first magnetometer $330_1$ both the MEIS current signal and the interfering signal on the structure under test, as described above with respect to FIGS. 14 and 15. A second magnetometer $330_2$ is placed over the second pipe which does not have any MEIS currents, but has comparable interference current.

The signal from one of the magnetometers (e.g., the second magnetometer $330_2$ shown in FIG. 16) can be phase shifted, if necessary, by using a constant amplitude phase-shift bridge 1604, and/or weight adjusted (e.g., scaled) at 1502, to provide an equal but opposite interference signal with respect to the output signal from the first magnetometer $330_1$. In any case, the two signals from the magnetometers $330_1$ and $330_2$ are summed at combiner 1504 to cancel or reduce the interfering signal component, such that the resultant MEIS leakage current component is passed to the processing circuitry of the MEIS subsystem 300 for further processing, as described above with respect to FIG. 3.

Bulk Pipe-to-Soil Impedance Spectroscopy

It has also been observed during field trials of the present invention that an alternate impedance measurement can be of additional value in characterizing pipelines. This is the impedance spectrum of the pipe-to-soil circuit for the complete pipe length driven by the MEIS signal source. This length extends on either side of the injection point for distances determined by the test frequency.

This spectrum, designated "Bulk Pipe-to-Soil Impedance Spectroscopy (BPIS)", can be useful in identifying gross anomalies in the coatings or large holidays. The primary analysis procedure involves comparison of the data with that from a known good pipe in the same locale. The spectrum can be viewed in either Nyquist or Bode plots as discussed above with respect to FIGS. 9A-9F.

BPIS can be measured in various modes to provide information characterizing the condition of the pipeline. One embodiment includes measuring the net impedance between the pipe and system ground-return electrode (BPIS1). An alternative embodiment includes measuring the net impedance between the pipe and soil (BPIS2). Taking the difference of BPIS1 and BPIS2 will show the value of the earthing resistance of the system ground-return electrode. BPIS generally uses the same test frequencies and MEIS.

Figure 17:
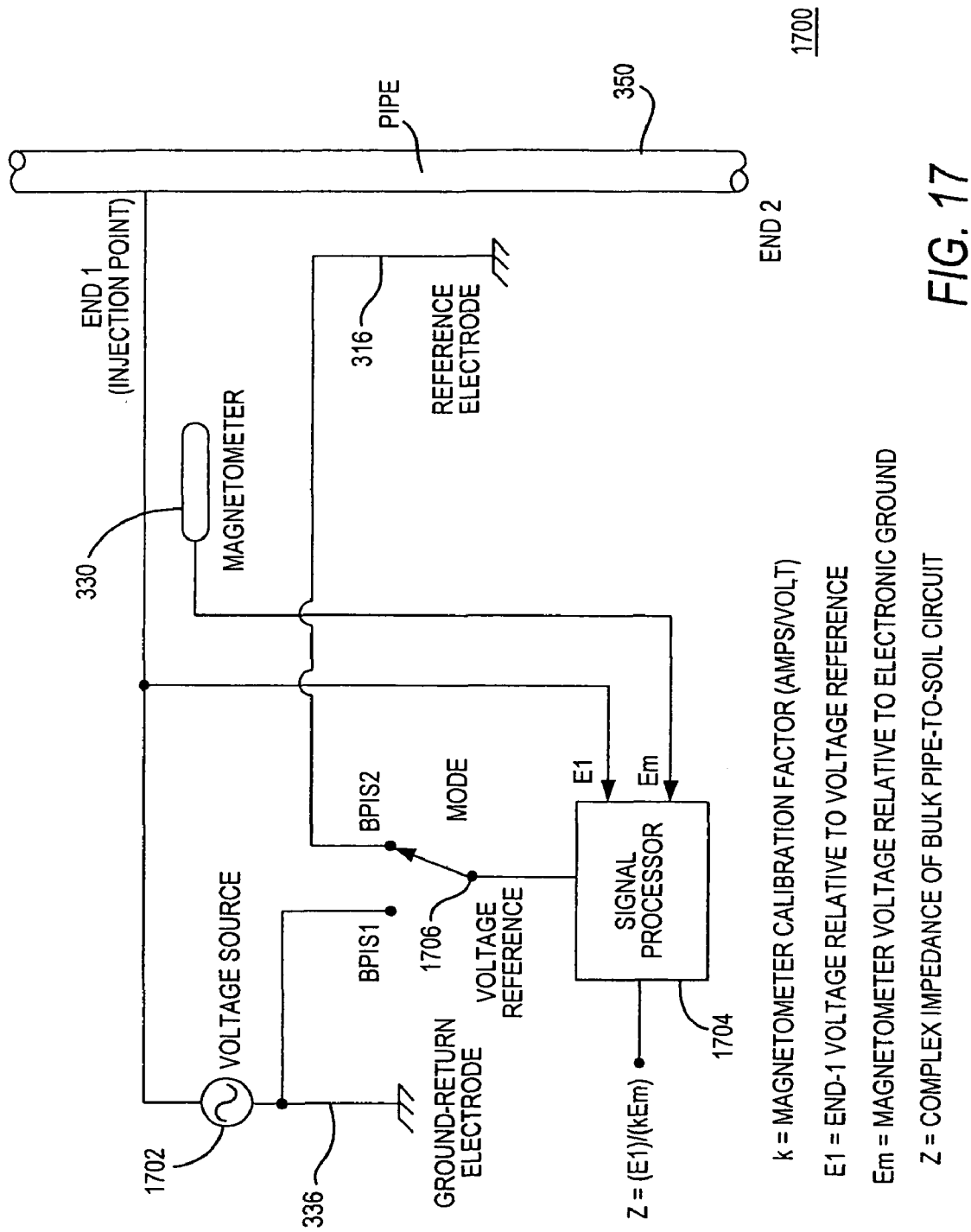
FIG. 17 is a schematic circuit diagram of a circuit for generating a bulk pipe-to-soil impedance spectroscopy (BPIS) frequency spectrum.

FIG. 17 illustrates the system connections 1700 for performing the impedance measurements. Voltage source 1702 is coupled between the ground-return electrode 336 and an injection end point (End-1) of the pipe 350. The reference electrode 316 is positioned proximate the pipe 350. The signal processor 1704 receives a signal E1 representing the End-1 voltage relative to the voltage reference 1706 and a signal $E_m$ representing the magnetometer voltage relative to the electronic ground.

In particular, BPIS1 is the vector sum of the BPIS2 impedance (net impedance between pipe and soil) and the earthing resistance of the ground-return electrode 336. BPIS1 acquires the voltage between the pipe 350 and the ground-return electrode 336, which is also the system output voltage. BPIS2, however, acquires the actual pipe-to-soil voltage as measured between the pipe 350 and the reference electrode 316. The impedance (Z) is computed by the signal processor 1704 in either BPIS1 mode or BPIS2 mode and is defined by the equation $Z=(E1)/(kE_m)$, where k is the magnetometer calibration factor (amps/volt).

One difference between MEIS and BPIS is that the magnetometer 330 is placed adjacent to the line feeding End-1 352 of a pipe segment 350. It therefore senses all the current delivered to the pipe.

One method related to BPIS is described in aforementioned U.S. Pat. No. 5,126,654 to Murphy et al., where the magnetometer is placed over the buried object to sense on-object current. This will sense only a portion of the feed current to the pipeline since current flows both directions away from the injection point on the pipe. Since there is no way to detect values for the current splitting without further measurement, this method will not provide bulk impedance values for the pipeline.

By contrast, the method of the present invention senses the net current fed to the pipeline because the magnetometer is placed over the feed line. As a result, BPIS produces direct impedance measurements of the pipe-to-soil circuit at the test site. This data may be useful in quantifying coating parameters.

Magnetometer calibration is accomplished in the manner described above by passing a known current through the feed line. This produces the complex calibration factor (k) for each frequency.

Down-Pipe Transmission Spectroscopy

It has been observed that soils with subsurface saltwater can adversely alter the measurements of the MEIS subsystem in terms of both attenuation and phase shift between the injection point (End 1) and the next cathodic protection (CP) test point (End 2). This indicates that the current is being leaked off the pipe in a distributed manner similar to propagation in a transmission line. This also means that standard MEIS may be impractical in these types of soil conditions because the pipe voltage at the test segment can not be inferred by measuring the End 2 voltage. The present invention provides an alternative approach to estimate the voltage at the MEIS test segment location.

In particular, the present invention provides a Down-Pipe Transmission Spectroscopy (DPS) technique to provide useful information at these locations. DPS measures the attenuation and phase shift of the End 2 voltage relative to that of End 1 of the pipe. This characterizes the distributive behavior of the pipe over the selected frequency spectrum. The benefits of DPS include the ability to characterize individual CP-to-CP test location spans of pipeline relative to each other; detection of micro-cracking or holidays; and estimation of actual pipe-to-soil voltage at the MEIS test site.

Figure 18:
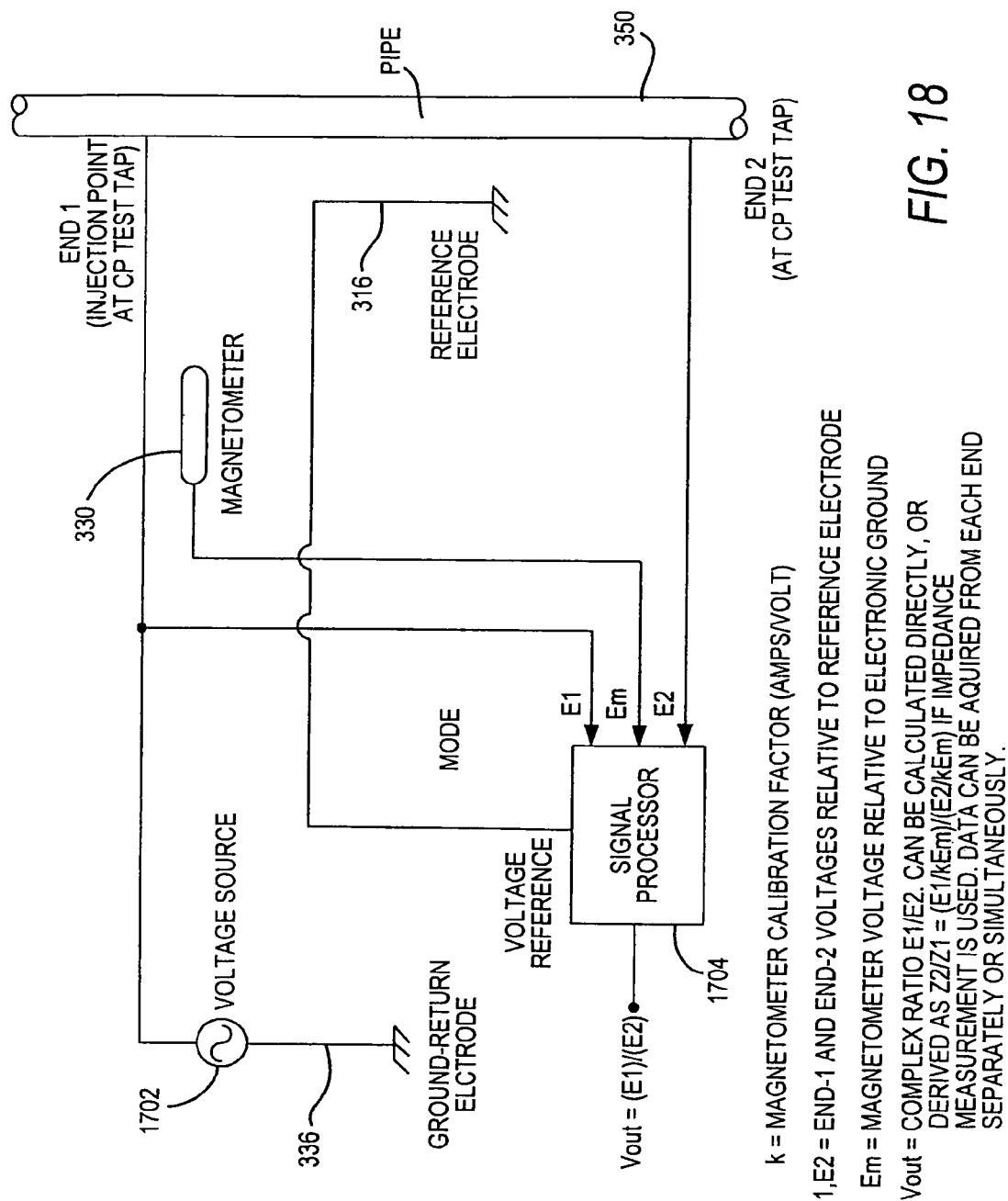
FIG. 18 is a schematic circuit diagram of a circuit for generating a down-pipe transmission spectroscopy frequency spectrum.

FIG. 18 is a schematic circuit diagram of a circuit 1800 for generating a down-pipe transmission spectroscopy frequency spectrum. The MEIS system 300 is connected to the pipe and soil as described above. However, the magnetometer 330 is maintained in one position for all readings. The magnetometer 330 can be located either above the pipe or adjacent to the End-1 feed line. The pipe end voltages $E_1$ (from End 1) and $E_2$ (from End 2) are acquired, along with magnetometer voltage Em. Data presentation is as follows: the phase shift and amplitude of $E_2$ relative to $E_1$ are calculated and plotted against frequency in a Bode plot.

The same impedance measurement procedure used in the present MEIS system as described above with respect to FIG. 3 is also employed for DPS. However, the system is equipped with a switch to select the MEIS voltage from either End 1 or End 2. Thus, one impedance data file is gathered from each end of the pipe section. In contrast, the MEIS mode of operation generally obtains its voltages only from End 2, and the two voltages measured therein ($V_1$ and $V_2$) correspond to magnetometer positions 1 and 2.

Accordingly, the impedances $Z_1=E_1/I$ and $Z_2=E_2/I$ are measured, where current (I) is the same in both cases since the magnetometer 330 is stationary. The desired vector quantity $E_2/E_1$ is therefore equal to $Z_2/Z_1$. This quantity, expressed in polar coordinates for each frequency, can be presented in the desired Bode plot. Alternatively, the Cartesian coordinates of each point can be presented in a Nyquist plot.

An alternative method for performing DPS includes measuring the pipe end voltages only and calculating their complex ratio, independent of current measurements. It is noted that the impedance measurement technology of the system potentiostat described above with respect to FIG. 3 lends itself well to this application.

Prediction of coating condition can be performed by comparing the DPS data against that of known good pipe in the same locale, or against a database of responses from a pipe with known anomalies, such as the pipe calibration samples described with respect to FIG. 4.

It has been observed that differing amplitude and phase values between End 1 and End 2 voltages can preclude the use of MEIS. This is because the actual pipe-to-soil voltage at the MEIS test site (between End 1 and End 2) is not known. DPS can alleviate this condition. Estimation of actual pipe-to-soil voltage at the test site can be performed by propagating an end-voltage spectrum to the test site using transmission line theory. This will facilitate successful MEIS testing at the site.

Specifically, the MEIS test site voltage can be estimated by first calculating the attenuation and phase shift factors per unit length of the pipe section, using the DPS numbers for the whole pipe section. These numbers can then comprise a complex propagation constant for the pipe section similar to that of electric transmission lines, from which the End 1 voltage can be forward-propagated, or the End 2 voltage can be back-propagated, to the actual MEIS test site location.

While the disclosed methods and apparatus have been particularly shown and described with respect to the preferred embodiments, it is understood by those skilled in the art that various modifications in form and detail may be made therein without departing from the scope and spirit of the invention. Accordingly, modifications such as those suggested above, but not limited thereto are to be considered within the scope of the invention, which is to be determined by reference to the appended claims.

We claim:

1. An electronic pipeline simulator for simulating electrical pipe-to-soil impedance of a coated segment of a pipeline, said electronic pipeline simulator operable without electrical or physical connectivity to an actual coated pipeline segment, and operable during calibration or testing of a magnetically-detected electrochemical impedance spectroscopy (MEIS) system, said electronic pipeline simulator comprising:
    a voltage excitation point for providing current to a first test point, said voltage excitation test point simulating the location where a pipe segment is electrically accessed, and said first test point representing an up-pipe location along the segment of pipeline where a first magnetometer measurement of said MEIS system is taken between the up-pipe location and ground;
    a leakage current circuit electrically coupled to the voltage excitation point and ground, the leakage current circuit comprising:
        a first RC circuit electrically coupled to the voltage excitation point and including a first capacitor in parallel with one of a plurality of resistive elements, each of the resistive elements being selectable by an operator and having different resistive values representing different bond conditions of the coated segment of the pipeline; and
        a soil condition resistive element coupled to the first RC circuit and ground, the soil condition resistive element comprising a plurality of resistive values that are selectable by the operator, each resistive value representing a different soil environment interfacing with the coated segment of a pipeline, wherein first RC circuit and the soil condition resistive element simulate a leakage current from the coated segment of a pipeline to ground; and
    a second test point electrically coupled to the leakage current circuit and representing a down-pipe location along the segment of pipeline where a second magnetometer measurement of said MEIS system is taken between the pipeline segment and ground, and wherein a current value derived from the second magnetometer measurement at the second test point equals a current value derived from the first magnetometer measurement at the first test point, less the current flowing through the leakage current circuit, and thereby facilitating calculation of current flowing through the leakage current circuit.

2. The electronic pipeline simulator of claim 1, wherein the resistive elements of the first RC circuit comprise a resistor, an open circuit and a short circuit, wherein the resistor represents a normal bond between the pipeline and the coating, the open circuit represents a disbond between the pipeline and the coating, and the short circuit represents a holiday between the pipeline and the coating.

3. The electronic pipeline simulator of claim 1, wherein the plurality of resistive values of the soil condition resistive element comprise a first resistance value, at least one second resistance value that is greater than the first resistance value, and an open circuit.

4. The electronic pipeline simulator of claim 3, wherein the first test point comprises:
    a current-sensing resistor coupled between the voltage excitation point and the leakage current circuit; and
    a first operational amplifier having first and second inputs respectively coupled to first and second ends of the sensing resistor, and an output forming the first test point, wherein a voltage at the output is proportional to the current provided at the current injection point.

5. A test circuit apparatus for simulating electrical pipe-to-soil impedance of a coated segment of a pipeline without actual or electrical connectivity to a coated pipeline segment, the apparatus comprising:
    means for providing a voltage excitation point in a test circuit that simulates a voltage excitation point on a buried pipe section;
    means for providing a first measuring location in the test circuit for measuring a first output signal with a magnetometer, said first measuring location having circuitry coupled to the voltage excitation point and simulating an up-pipe location over the buried pipe section;
    means for providing a second measuring location in the test circuit for measuring a second output signal with the magnetometer, said second measuring location having circuitry coupled to the voltage excitation point and simulating a down-pipe location over the buried pipe section;
    means for providing an RC circuit in the test circuit, the RC circuit having selectable resistive elements for simulating various bonding conditions of pipe coating of the pipe section, said RC circuit being electrically coupled to the voltage excitation point; and
    means for providing a soil resistance circuit in the test circuit, the soil resistance circuit being serially coupled between the RC circuit and ground, said soil resistance circuit having selectable resistive elements for simulating various soil resistance values of a soil environment surrounding the buried pipe section.

6. The test circuit apparatus of claim 5, wherein the selectable resistive elements of the RC circuit comprise a resistor, an open circuit and a short circuit, wherein the resistor represents a normal bond between the pipeline and the coating, the open circuit represents a disbond between the pipeline and the coating, and the short circuit represents a holiday between the pipeline and the coating.

7. The test circuit apparatus of claim 5, wherein the selectable resistive elements of the soil resistance circuit comprise at least two resistors having progressively increasing resistance values.

8. A method for simulating electrical pipe-to-soil impedance of a coated segment of a pipeline without actual or electrical connectivity to a coated pipeline segment, the method comprising the steps of:
    providing a voltage excitation point in a test circuit that simulates a voltage excitation point on a buried pipe section;

providing a first measuring location in the test circuit for measuring a first output signal with a magnetometer, said first measuring location having circuitry coupled to the voltage excitation point and simulating an up-pipe location over the buried pipe section;

providing a second measuring location in the test circuit for measuring a second output signal with the magnetometer, said second measuring location having circuitry coupled to the voltage excitation point and simulating a down-pipe location over the buried pipe section;

providing an RC circuit in the test circuit, the RC circuit having selectable resistive elements for simulating various bonding conditions of pipe coating of the pipe section, said RC circuit being electrically coupled to the voltage excitation point; and providing a soil resistance circuit in the test circuit, the soil resistance circuit being serially coupled between the RC circuit and ground, said soil resistance circuit having selectable resistive elements for simulating various soil resistance values of a soil environment surrounding the buried pipe section.

* * * * *